(12) United States Patent
Deng et al.

(10) Patent No.: US 9,637,797 B2
(45) Date of Patent: May 2, 2017

(54) METHODS AND NUCLEOTIDE FRAGMENTS OF PREDICTING OCCURRENCE, METASTASIS OF CANCERS AND PATIENTS' POSTOPERATIVE SURVIVAL IN VITRO

(75) Inventors: Dajun Deng, Beijing (CN); Jun Zhang, Beijing (CN); Zhaojun Liu, Beijing (CN); Jing Zhou, Beijing (CN); Liankun Gu, Beijing (CN); Baozhen Zhang, Beijing (CN)

(73) Assignee: Beijing Institute For Cancer Research, Beijing (CN)

( * ) Notice: Subject to any disclaimer, the term of this patent is extended or adjusted under 35 U.S.C. 154(b) by 0 days.

(21) Appl. No.: 14/378,285

(22) PCT Filed: Feb. 13, 2012

(86) PCT No.: PCT/CN2012/000169
§ 371 (c)(1),
(2), (4) Date: Aug. 12, 2014

(87) PCT Pub. No.: WO2013/120222
PCT Pub. Date: Aug. 22, 2013

(65) Prior Publication Data
US 2016/0040243 A1    Feb. 11, 2016

(51) Int. Cl.
C12Q 1/68 (2006.01)
C12P 19/34 (2006.01)
C07H 21/02 (2006.01)
C07H 21/04 (2006.01)
G06F 19/22 (2011.01)

(52) U.S. Cl.
CPC ...... *C12Q 1/6886* (2013.01); *C12Q 2600/112* (2013.01); *C12Q 2600/118* (2013.01); *C12Q 2600/154* (2013.01); *C12Q 2600/158* (2013.01); *G06F 19/22* (2013.01)

(58) Field of Classification Search
None
See application file for complete search history.

(56) References Cited

U.S. PATENT DOCUMENTS

| | | | | |
|---|---|---|---|---|
| 2008/0213791 A1* | 9/2008 | Freije | ............ | C12Q 1/6886 435/6.12 |
| 2009/0215709 A1* | 8/2009 | Van Criekinge | ..... | C12Q 1/6886 514/34 |
| 2013/0296328 A1* | 11/2013 | Fuks | ............ | C12Q 1/6886 514/249 |

FOREIGN PATENT DOCUMENTS

| | | |
|---|---|---|
| CN | 102140498 A | 8/2011 |
| EP | 2537941 A1 | 12/2012 |
| WO | WO-2010/086388 A1 | 8/2010 |
| WO | WO-2013/120222 A1 | 8/2013 |

OTHER PUBLICATIONS

Smiraglia (Human Molecular Genetics. 2001. 10: 1413-1419.*
(Continued)

*Primary Examiner* — Carla Myers
(74) *Attorney, Agent, or Firm* — Schwegman Lundberg & Woessner, P.A.

(57) ABSTRACT

Provided in the present invention are a method using in vitro measurement of the content of methylation or demethylation of GFRa1 CpG islands to estimate a risk of tumorigenesis and of tumor metastasis, or postoperative life expectancy, and a nucleotide sequence used.

8 Claims, 10 Drawing Sheets

(56) References Cited

OTHER PUBLICATIONS

Okada et al (Genes, Chromosomes & Cancer. Published online Feb. 5, 2010. 49: 452-462.*
Boers et al. Clinical Epigenetics. 2016. 8:29.*
Koh et al Tumor Biology. Published online Feb. 11, 2016, pp. 1-10.*
Sato et al. PLoS One 8(3): e59444.*
Battagli et al. Cancer Research. Dec. 2003. 63: 8695-8699.*
Ushijima et al Nature Reviews. 2005. 5: 223-231.*
Ehrlich et al. Oncogene 2002. 21: 5400-5413.*
Godmann et al. PLos One. Sep. 14, 2010. 5(9): e12727.*
Godmann et al PLos One. Sep. 14, 2010. 5(9): e12727 and supplemental Table S2.*
"International Application Serial No. PCT/CN2012/000169, International Preliminary Report on Patentability dated Aug. 19, 2014", (w/ English Translation), 10 pgs.
"International Application Serial No. PCT/CN2012/000169, International Search Report mailed Nov. 29, 2012", (w/ English Translation), 6 pgs.
"International Application Serial No. PCT/CN2012/000169, Written Opinion mailed Nov. 29, 2012", (w/ English Translation), 8 pgs.
Airaksinen, Matti S., et al., "The GDNF Family: Signalling, Biological Functions and Therapeutic Value", *Nature Reviews Neuroscience*, 3, (May 2002), 383-394.
Esseghir, Selma, et al., "A Role for Glial Cell-Derived Neurotrophic Factor-Induced Expression by Inflammatory Cytokines and RET/GFR a1Receptor Up-regulation in Breast Cancer", *Cancer Res.*, 67(24), (2007), 11732-11741.
Jing, Shuqian, et al., "GDNF-Induced Activation of the Ret Protein Tyrosine Kinase Is Mediated by GDNFR-α, a Novel Receptor for GDNF", *Cell*, 85(7), (1996), 1113-1124.
Liu, Z., et al., "Zhong liu huan zi xiang guan DNA jiajihua biao zhi wu yan jiu jin zhan", *Journal of Medical Research*, 39(12), (2010), 135-138.
Sawai, Hirozumi, et al., "The G691S RET Polymorphism Increases Glial Cell Line-Derived Neurotrophic Factor-Induced Pancreatic Cancer Cell Invasion by Amplifying Mitogen-Activated Protein Kinase Signaling", *Cancer Res*, 65(24), (2005), 11536-11544.
Watanabe, Y., et al., "Sensitive and Specific Detection of Early Gastric Cancer with DNA Methylation Analysis of Gastric Washes", *Gastroenterology*, 136(7), (2009), 2149-2158.
Widschwendter, Martin, et al., "Association of Breast Cancer DNA Methylation Profiles with Hormone Receptor Status and Response to Tamoxifen", *Cancer Res.*, 64(11), (2004), 3807-3813.

\* cited by examiner

SEQUENCE LISTING

<160> NUMBER OF SEQ ID NOS: 17

<210> SEQ ID NO 1
<211> LENGTH: 2567
<212> TYPE: DNA
<213> ORGANISM: Artificial Sequence
<220> FEATURE:
<223> OTHER INFORMATION: A synthetic oligonucleotide

<400> SEQUENCE: 1

```
gggauauuat tguuutgaaa gaataaataa gtaaataaau aaautggutu utcgucguag      60
utggacgcgg tcggttgagt uuaggttggt gguatttgga gttttttttcg ttutgtttgg     120
gaauuuattg ucguttuucg tuuututtuu uuautuuttu ttuuuuuutu utucgguuau     180
uuutttuttt ttgutggcgt utuuuaautt taggguucgg ggggcgutcg tggcgucggg     240
utguauutgu cggggguacgu cgggautgcg ggucggcgcg utcguuutgg gutgggtgc     300
ggaagcguuc gagtuutggg uaucgggcga gagtgtgaga ggagcggacg uuuaggaggg     360
agucgaggac gcgcggcggg tagggggtag gggcguagga aucgggttttu aguuuuagtc     420
gggauatcgg ttuuuuutgg uttggcgguu tutgaggga gacgagtuuc ggggagaagg     480
agggcggcga utgggutag ggattggcga tcggagtggg gagggucggc ggutgagcga      540
gutcgutggu tgacgcgagg aggggaggu uaauttuucg ggagaagggg ututttcggc     600
guuagggutg gutagggagu tgucgucguc guuaucgagg gutcggautu uagguagutg     660
uaggutucgu tcgcgacgut cggaaagtau cgtttattta tttatttgut tgcgttuagc    720
gtutcgggtt gaauuuaaua gauauuuuut tggautttag gaauuututt uagauututu     780
uaguuuutau utuuatuuuc gtgtuagcgg uuuutgaaa auacguauat guauuucgau      840
utgggtgggg gtgggtuutu auuucggtgt tggaaattuu uuaaaggcgg gaacggggga     900
ggggagaggg ttutgtgggg ggagtutucg gcgututucg ututuatutu aaagcgcguu     960
utuuuttuua ggttgggtcg gauutgaauu uutaaaagcg gaaucguutu ucguuutcgu    1020
uatuucggag utgagtcguc ggcggcggtg gutgutguua gauucggagt ttuututttu    1080
autggatgga gutgaauttt gggcgguuag aguaguauag utgtucgggg atcgutguac    1140
gutgagutuu utcgguaaga uuuagcggcg gutcgggatt ttttgggg ggcggggauu      1200
aguuucgcgu cgguauuatg ttuutggcga uuutgtautt cgcgutgucg utuutgggta    1260
agtcgagguu cgucgcgggu tttuttauuu tutgagtutt tuutagggtc guttguagua    1320
guuuauuucg uuutucguau uaaaattggg gcgcgggtgt ggtggatgtg gaaggaagaa    1380
gtgtutttttt ggggaatggg atcgcgaatu uucggggttag ggaggcggtg gcggcgcggc 1440
```

| | |
|---|---|
| gutguutgaa guttttcggg uttggttttg atttuutgtg gtttttaatg auuuaauttg | 1500 |
| gcggggaut aagaaguuut uuaguuuagg guuutguauu uuuagagagt ututgggagu | 1560 |
| tcgcggaguc gcggcgggua ggtggagttg gggaguattg gggucgggag aguaaauttg | 1620 |
| gaagagaaaa gtttttuucg agtaguttut ggguaututu cguucggcgg aucgutgauu | 1680 |
| atggutgguu tguuucgcgu uuagcgcgcg uucggtguuu agtucgucgu cguauttutu | 1740 |
| utcggaaagc guutgagttt uagucgggcg gagcgggtgg utggagucgg gggtgguucg | 1800 |
| ggaguucggg tcgttgutua gguuaggatg uuucggggcg gagggucgac gtgcgcggtg | 1860 |
| ggtagcguag gututggagu aaauuuttga aguucgcggg utgaguutgc guuaututtu | 1920 |
| uttgcggguu cggaggagg agagaggagu tggaattuua gggggcggga aaatggautu | 1980 |
| ucggatggtc gagaggtgga uucgutuuua gaguagggcg uuucgaagg utggtuaagu | 2040 |
| atuuutgauu cgggcgcgcg uuutcguucg gaguaggggc ggucggggtu uucguucguc | 2100 |
| guautaggu tuuutuuuut utguuucgua gauttgutuu tgtcggucga agtgagcggc | 2160 |
| ggagaucguu tggattgcgt gaaaguuagt gatuagtguu tgaaggagua gagutgagu | 2220 |
| auuaagtauc guacgutaag guagtgcgtg gcggguaagg agauuaautt uaguutggua | 2280 |
| tucgguutgg agguuaagga tgagtgucgu agcguutgg agguuutgaa guagaagtcg | 2340 |
| ututauaaut gucgutguaa gcggggtatg aagaaggaga agaautguut gcguatttau | 2400 |
| tggaguatgt auuagaguut guagggtacg cgtggaauut uuuuauuuua uuucgtgtuu | 2460 |
| utuuucgaag guaggcgggu utttcgtuuu tgggtuagut gatutuatuu tuuautuaut | 2520 |
| tutuuuuagu tguagagtga ggautttuu ttgguuuuua gggauaa | 2567 |

<210> SEQ ID NO 2
<211> LENGTH: 2567
<212> TYPE: DNA
<213> ORGANISM: Artificial Sequence
<220> FEATURE:
<223> OTHER INFORMATION: A synthetic oligonucleotide

<400> SEQUENCE: 2

| | |
|---|---|
| gggauauuat tguuutgaaa gaataaataa gtaaataaau aaautggutu utuguuguag | 60 |
| utggaugugg tuggttgagt uuaggttggt gguatttgga gttttttttug ttutgtttgg | 120 |
| gaauuuattg uuguttuuug tuuututtuu uuautuuttu ttuuuuutu utuggguuau | 180 |
| uuutttuttt ttgutggugt utuuuaautt tagggutugg ggggugutug tggutuuggg | 240 |
| utguauutgu uggguaugu ugggautgug gguggutgug utguuutgg gutgggtgu | 300 |
| ggaaguguuu gagtuutggg uauggguga gagtgtgaga ggaguggaug uuuaggaggg | 360 |
| aguugaggau gugugguggg taggggtag ggguguagga auuggguttu aguuuagtu | 420 |
| gggauatugg ttuuuuutgg uttggtgguu tutggagga gaugagtuuu ggggagaagg | 480 |
| aggguguga utggggutag ggattgguga tuggagtggg gagggutgu ggutgagtga | 540 |
| gutugutggu tgaugugagg aggggaggu uaauttuuug ggagaagggg ututttuggu | 600 |
| guuagggutg guaggagu tguuguguu guuatugagg gutuggautu uagguagutg | 660 |
| uaggutuugu tugugautgt tggaaagtau ugtttattta tttatttgut tgugttuagu | 720 |
| gtutugggtt gaauuuaaua gatauuuut tggautttag gaauuututt uagautututu | 780 |
| uaguuutuau utuuatuuuu gtgtuagugg uuuutgaaa auauguauat guauuuugau | 840 |
| utgggtgggg gtgggtuutu auuuuggtgt tggaaattuu uuaaggtggg gaatggggaa | 900 |
| ggggagaggg ttutgtgggg ggagtutuug gugututuug ututuatutu aaaguguguu | 960 |

-continued

| | |
|---|---|
| utuuuttuua ggttgggtug gauutgaauu uutaaaagug gaauuguutu uuguuutugu | 1020 |
| uatuuuggag utgagtuguu ggugguggtg gutgutguua gauuuggagt ttuututttu | 1080 |
| autggatgga gutgaauttt gggugguuag aguaguauag utguuugggg augugutguau | 1140 |
| gutgagutuu utgguaaga uuuagugguguug gutugggatt ttttgggggg ggugggggauu | 1200 |
| aguuugugu ugguauuatg ttuutgguga uuutguautt ugugutguug utuugggta | 1260 |
| agtugagguu ugugugggu tttuuttauuu tutgagtutt tuutagggtu guttguagua | 1320 |
| guuuauuug uuutuuguau uaaaattggg guguggtgt ggtggatgtg gaaggaagaa | 1380 |
| gtgtuttttt ggggaatggg atugugaatu uuugggttag ggagguggtg gugguguggu | 1440 |
| gutguutgaa guttttuggg uttggttttg atttuutgtg gttttaatg auuuaauttg | 1500 |
| guggggaut aagaaguuut uuaguuuagg guuutguauu uuuagagagt ututgggagu | 1560 |
| tuguggaguu gugguggua ggtggagttg gggaguattg ggguugggag aguaaauttg | 1620 |
| gaagagaaaa gttttttuuug agtaguttut ggguauutu uguuuggugg auugutgauu | 1680 |
| atggutgguu tguuugugu uuagugugug uuggtguuu agtuuguugu uguauttutu | 1740 |
| utuggaaagu guutgagttt uaguuggggug gaguggtgg utggaguugg gggtgguuug | 1800 |
| ggaguuggg tugttgutua gguuaggatg uuuuggggug gaggguugau gtguguggtg | 1860 |
| gguaguguag gututggagu aaauuuttga aguuuguugg utgaguutgu guuaututtu | 1920 |
| uttgugggguu ugggaggagg agagaggagu tggaattuua ggggguggga aaatggautu | 1980 |
| uuggatggtu gagaggtgga uuugutuuua gaguagggug uuuuugaagg utggtuaagu | 2040 |
| atuuutgauu ugggugugug uuutguuug gaguagggu gguugggtu uuguuugutu | 2100 |
| guautuaggu tuuutuuuut utguuuugua gauttgutuu tgtugguuga agtgagtggu | 2160 |
| ggagauugu tggattgugt gaaaguuagt gatuagtguu tgaaggagua gagutguagu | 2220 |
| auuaagtauu guaugutaag guagtgugtg gugggguaagg agauuaauutt uaguuggua | 2280 |
| tuugguutgg agguuaagga tgagtguugu aguguuatgg agguutgaa guagaagtug | 2340 |
| ututauaaut guugutguaa guggggtatg aagaaggaga agaautguut guguatttau | 2400 |
| tggaguatgt auuagaguut guagggtaug ugtggaauut uuuuauuuua uuuugtguu | 2460 |
| utuuuugaag guaggugggu utttugtuuu tgggtuuagut gatutuatuu tuuautuaut | 2520 |
| tutuuuuagu tguagagtga ggauutttuu ttgguuuuua gggauaa | 2567 |

<210> SEQ ID NO 3
<211> LENGTH: 2567
<212> TYPE: DNA
<213> ORGANISM: Artificial Sequence
<220> FEATURE:
<223> OTHER INFORMATION: A synthetic oligonucleotide

<400> SEQUENCE: 3

| | |
|---|---|
| ttgtuuutgg ggguuaagga aaggtuutua utugutguagut ggggagaagt gagtggagga | 60 |
| tgagatuagu tgguuuaggg acgaaaggguu cguutguutt cggggaggga uacggggtgg | 120 |
| ggtgggagg ttuacgcgt auuutguagg ututggtaua tgutuuagta aatgcguagg | 180 |
| uagtuttut uuttuttuat auuucguttg uagcgguagt tgtagagcga uttutguttu | 240 |
| aggguutuua tggcgutgcg guautuatuu ttgguutuua ggucggatgu uaggutgaag | 300 |
| ttggtutuut tguucguuac guautguutt agcgtgcggt auttggtgut guagututgu | 360 |
| tuuttaggu autgatauat ggutttuacg uaatuuaggc ggtutucguc gutuauttcg | 420 |

```
gucgauagga guaagtutgc gggguagagg ggagggaguu tgagtgcggc gggcggggau      480
uucggucguu uutgutucgg gcagggcgc gcguucgggt uagggatgut tgauuaguut       540 tcggggcgu uutgututgg gagcgggtuu auututcgau uatucgggag tuuattttuu       600
cguuuuutgg aattuuagut uututututuut uttuucgggu ucguaaggaa gagtggcgua    660
ggutuaguuc gcgggguttua agggtttgut uuagaguutg cgutguuuau cgcguacgtc    720
gguuutucgu uucggggguat uutgguutga guaacgauuc gggutuucgg guuauuuucg    780
gutuuaguua uucgutucgu ucggutgaaa utuaggcgut ttcgaggag aagtgcggcg      840 gcggautggg uaucgggcgc gcgutgggcg cggggguaggu uaguuatggt uagcggtucg    900
ucgggcggag agtguuuaga agutautcgg gaaaaauttt tutuuttuuaa gtttgututu   960 ucgguuuuaa tgututuuaa utuuauutgu ucgucgcggu tucgcagagut uuuagagaut    1020 ututgggggt guagggguut ggguutggagg guttuttagt uuuucguuaa gttgggguat    1080
taaaaauuau aggaaatuaa aauuaaguuc gaaaguuu agguagcguc gcgucguuau     1140
cguutuuuta auucggggat tcgcgatuuu attuuuaaa aagaaauttu ttuuttuuau     1200
atuauuauaa uucgcguuuu aattttggtg cggagggcgg ggtgggutgu tguaagcgau    1260
uutaggaaag autuagaggg taagaaaguu cgcggcgggu utcgauttau uuaagagcgg    1320
uagcgcgaag tauaggggtcg uuaggaauat ggtgucggcg cggggutggt uuucguuuuu   1380
uuaaaaaaat uucgagucgu cgutgggutut tgucgaggga gutaguatg uagcgatuuu    1440 cggauagutg tgutgututg gucguuuaaa gttuagutuu atuuagtgaa agaggaaaut    1500
ucgggtutgg uaguaguuau cgucgucggc gautuagutu cgggatggcg agggcgggag    1560
gcggttucgu ttttaggggt uaaggtucga uuuaauutgg aagggagggc gcgutttgag    1620 atgagagcg agagcgucgg agautuuuuu uauagaauuu tutuuutuu uucgttuucg      1680 uutttgggga atttuuaaua ucggggtgag gauuuauuuu uauuuaggtc ggggtguatg    1740
tgcgtgtttt uuaggggtcg utgauacggg gatggaggtg aggguggag aggtutgaag    1800 aggggttuuta aagtuuaagg gggtguutgt tgggttuaau ucgagacgut gaacguaagu   1860
aaataaataa ataaacggta utttucgagc gtcgcgagcg gaguutguag utguutggag    1920 tcgaguuut cggtggcggc ggcgguagut uuutaguuag uuutggcguc gaaagaguuu     1980
uttutuucgg gaagttgguu tuuuuutuut cgcguuaguu agcgagutcg utagucguc     2040 gguuutuuuu autcgatcg uuaatuuuta guuuuagtcg ucguuutuut tutuuucggg    2100
autcgtutuu utuuagaggu cguuaaguua gggggaaucg atgtuucgau tgggutgaa    2160 auucggtuu tgcguuuta uuuuutauuc gucgcgcgtu utcggutuuu tuutgggcgt     2220
ucgutuutut uauaututcg uucggtguuu aggtutcggg cguttcgua uuuuaguuua    2280 gggcgagcgc gutcgguucgu agtuucggcg tguuucggua ggtguaguuc ggcguuacga    2340 gcguuuucg gguuutaaag ttgggagacg uuaguaaaaa gaaagggggtg gucgaggag    2400 gggggaagaa ggagtgggga agagggacgg gaagcgguaa tgggttuuua aauagaacga   2460 aaaaaauuu aaatguuauu aauutggaut uaacgaucg cgtuuagutg cggcgaggag    2520
uuagtttgtt tatttautta tttattuttt uagggguaatg gtgtuuu              2567
```

<210> SEQ ID NO 4
<211> LENGTH: 2567
<212> TYPE: DNA
<213> ORGANISM: Artificial Sequence
<220> FEATURE:
<223> OTHER INFORMATION: A synthetic oligonucleotide

<400> SEQUENCE: 4

```
ttgtuuutgg ggguuaagga aaggtuutua ututguagut gggagaagt gagtggagga        60
tgagatuagu tgguuuaggg augaaagguu uguutguutt uggggaggga uauggggtgg      120
ggtggggagg ttuuaugugt auuutguagg ututggtaua tgutuuagta aatguguagg      180
uagttuttut uuttuttuat auuuuguttg uagugguagt tgtagaguga uttutguttu      240
agguuutuua tggugutgug guautuatuu ttgguutuua gguggatgu uaggutgaag      300
ttggtutuut tguuuguuau guatguutt agugtguggt auttggtgut guagututgu      360
tuuttuaggu autgatuaut ggutttuaug uaatuuaggu ggtutuuguu gutuauttug      420
guugauagga guaagtutgu ggggguagagg ggagggaguu tgagtguggu gggugggau      480
uuugguuguu uutgutuugg gugagggugu guguuuggt uagggatgut tgauuaguut      540
tuggggugu uutgututgg gagugggtuu auutututgau uatuugggag tuuattttuu      600
uguuuuutgg aattuuagut uututututuut utuuugggu uuguaaggaa gagtggugua      660
ggutuaguuu gugggguttua agggtttgut uuagaguutg ugtguuuau uguguaugtu      720
gguutuugu uuugggguat uutgguutga guaaugauuu gggutuugg guuauuuuug      780
gutuuaguua uuugutuugu uuggutgaaa utaaggugut ttugaggag aagtguggug      840
guggautggg uauggggugu gugtggggug uggggtaggu uagutatggt uaguggtuug      900
uugggtuggag agtguuuaga aguatutgg gaaaaauttt tututtuuaa gttgtututu      960
uugguuuaa tgtuuuuaa utuuauutgu uguuguggu tuugugagut uuuagagaut     1020
ututggggt guagggtuut gggutggagg guttuttagt uuuugtuuaa gttgggtuat     1080
taaaauuau aggaaatuaa aauuaaguuu gaaaguttu aggaguguu uguuguuau     1140
uguutuuuta auuuggggat tugugatuuu attuuuaaaa aagaaauttu ttuuttuuau     1200
atuuauuaua uuuuguuuu aatttttggtg uggaggugg ggtggggtgu tguaagugau     1260
uutaggaaag autuagaggg taagaaaguu uguggugggu utugauttau uuaagaguggg    1320
uagugugaag tauagggtug uuaggaauat ggtguuggug ugggtggt uuuguuuu     1380
uuaaaaaat uugagutgu ugtggggtut tguuaggga gutaguatg uagugatuuu     1440
uggatagutg tgutgututg guuguuuaaa gtuagutuu atuuagtgaa agaggaaaut     1500
uugggtutgg uagtaguuau uguugutgu gautuagutu tugggatggug agggugggag     1560
guggtuugu tttaggggt uaggtuuga uuuaauttgg aagggagggt gugutttgag     1620
atgagagugg agagtguugg agautuuuuu uauagaauuu tutuuuutuu uuugttuuug     1680
uutttgggga atttuuaaua uggggtgag gauuuauuuu uauuuaggtu ggggtguatg     1740
tgugtgtttt uuagggguug utgatauggg gatggaggtg agggtggag aggtutgaag     1800
agggttuuta aagtuuaagg gggtgtutgt tgggttuaau uugagaugut gaaugtaagu     1860
aaataaataa ataaauggta utttuugagu gtgugagug gaguutguag utguutggag     1920
tuugaguuut uggtgguggu ggtguagutt uuutaguuag uuutgutguu gaaagagutuu     1980
uttutuuugg gaagttgguu tuuuutuut ugtugtuagtu agugagutug utaguutguu     2040
gguutuuuu autugatug uuaatuuuta guuuagtug tugutuuut tutuuuutggg     2100
autugtutuu utuuagaggu tguuaaguua ggggggaauug atgtuuugau tgggutgaa     2160
auuuggttuu tguguuuta uuuuutauuu guugugugtu utggtututu tuutgggugt     2220
uugtuutut uauautututg uuuggtguuu aggtutuggg uguttuugua uuuuaguuua     2280
```

```
gggugagugu guugguuugu agtuuuggug tguuuuggua ggtguaguuu ggguguuauga    2340 guguuuuuug ggguuuaaag uugggagaug uuaguaaaaa gaaaggggug guuggaggag    2400 ggggaagaa ggagugggga agagggaugg gaagugguaa uggguuuuua aauagaauga    2460
aaaaaautuu aaauguuauu aauuuggauu uaauugauug ugutuagug uggugaggag    2520 uuagutugut tatttautta tttattuttt uaggguaaug gugutuuu                2567
```

<210> SEQ ID NO 5
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 5

```
ggtgttggaa atttttaaa gg                                              22
```

<210> SEQ ID NO 6
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 6

```
aaaacacttc ttccttccac at                                             22
```

<210> SEQ ID NO 7
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 7

```
agttttttt tttattggat ggagttg                                         27
```

<210> SEQ ID NO 8
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 8

```
cctaaactaa aaaacttctt aatccc                                         26
```

<210> SEQ ID NO 9
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 9

```
ggattagttt cgcgtcggta                                                20
```

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 10

```
cgccccaatt ttaatacgaa                                              20

<210> SEQ ID NO 11
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 11
gcgattttgt atttcgcgtt                                              20

<210> SEQ ID NO 12
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 12
ggggtgggga ttagttttgt                                              20

<210> SEQ ID NO 13
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 13
acacccacac cccaatttta                                              20

<210> SEQ ID NO 14
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 14
tgaggtttgt tgtgggtttt t                                            21

<210> SEQ ID NO 15
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 15
tctaacaatt ataaactcca accaccaa                                     28

<210> SEQ ID NO 16
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 16
gggaagatgg gatagaaggg aatat                                        25

<210> SEQ ID NO 17
<211> LENGTH: 36
<212> TYPE: DNA
```

```
<213> ORGANISM: Artificial Sequence
<220> FEATURE:
<223> OTHER INFORMATION: A synthetic oligonucleotide

<400> SEQUENCE: 17
ccttcattct aacccaatac ctatcccacc tctaaa                              36
```

METHODS AND NUCLEOTIDE FRAGMENTS OF PREDICTING OCCURRENCE, METASTASIS OF CANCERS AND PATIENTS' POSTOPERATIVE SURVIVAL IN VITRO

PRIORITY APPLICATIONS

This application is a U.S. National Stage Filing under 35 U.S.C. 371 from International Application No. PCT/CN2012/000169, filed on 13 Feb. 2012, and published as WO 2013/120222 on 22 Aug. 2013; which application and publication are incorporated herein by reference in their entirety.

TECHNICAL FIELD

The present invention relates to methods of predicting the ability of malignant tumor invasion, metastasis in vitro and length of patients' survival time, and also relates to the nucleotide fragments used in the methods.

TECHNICAL BACKGROUND

Invasion and metastasis are predominantly reasons for the poor prognosis of cancers. Destructions of the neighbor and distant organs by cancer invasion and metastasis lead to loss of chance for surgical resection and recurrence after curative treatments. Sensitive biomarkers for detection of potential of invasion and metastasis would greatly improve the personalized clinical management for cancer patients. Therefore, predicting the invasion and metastasis potential of cancers is eagerly awaited.

It is well recognized that it is virtually impossible to identify metastasis potential of cancers based on histopathologic grounds alone. So it is expected to make molecular subtyping using the molecular biology methods. Great progress has been achieved on the expression change of protein and RNA in the past decades. Although there are many studies on cancer biology, the effectual method is still unavailable to accurately recognize the metastasis ability of cancer cells.

As the rapid development of molecular biology, people have got a comprehensive understanding on the mechanisms of carcinogenesis. In addition to the genetic inactivation or activation of tumor related genes (including p53, APC and Ras, etc.), epigenetic inactivation of tumor suppressor genes (including p15, p16 and hMLH1, etc.) by hypermethylation and reactivation of proto-oncogenes by hypomethylation of CpG islands are other kinds of frequent events in cancers. It is well known that detection of alterations of protein levels and mRNA levels of genes in a few abnormal cells in tissue samples is very difficult using regular gene expression assays, because their visibility would be greatly reduced by the co-existence of main cell populations in which the gene expression has not changed. In contrast, methylated and demethylated CpG islands can be analyzed with methylation- and demethylation-specific assays, respectively. This makes the detection of the methylation status of CpG islands so sensitive that methylation alterations that occurred in a few cells in a testing tissue can be clearly displayed. This makes DNA methylation an optimal biomarker for molecular stratification of cancers.

Receptor GFRa1 combines with Glial cell line-Derived Neurotrophic Factor (GDNF), forming the phosphotyrosine kinase [Cell 1996, 85(7):1113-1124] of the oncogene RET which is capable of activating the signaling pathways such as SRC, MAPK, AKT and Rho, etc. It is closely related to the proliferation, differentiation and migration of the cells [Nature Reviews Neuroscience 2002, 3(5):383-394]. It has been discovered that GFRa1 expression is elevated in the tissues of a number of cancers (such as pancreatic cancer, breast cancer, olfactory cell carcinoma and the glial cell tumor). Elevated expression of this gene promotes the occurrence, development and metastasis of these cancers [Cancer Research 2005, 65(24):11536-11541; Cancer Research 2007, 67(24): 11733-11741]. It has also been reported that the methylation-deactivation of GDNF, the ligand of GFRa1, is related to the occurrence of gastric cancer [Gastroenterology 2009; 136:2149-2158]. But there is no report on the method of using the methylation and demethylation of GFRa1 CpG islands to estimate the occurrence, metastasis and survival of tumors.

DETAILED DESCRIPTION OF INVENTION

On one hand, the present invention provides an in vitro detection assay for the occurrence, metastasis, and survival time of tumor and the artificial nucleotide used in the method. It will help with the early discovery and definite diagnosis making of tumor, the accurate estimation of the metastasis ability of tumor and the postoperative survival time of patients to provide help for the diagnosis and treatment of tumor.

In order to obtain the above effectives, the invention provides the following technical proposal.

An in vitro detection assay for occurrence of tumor is disclosed in the invention, which including the following steps:
a) Extracting of genomic DNA or plasma free DNA samples from cancer patients and normal patients respectively;
b) Detecting and calculating proportion of methylation (or demethylation) of GFRa1 CpG islands, determining of a cutoff value of methylation (or demethylation) for tumor;
c) Extracting of genomic DNA or plasma free DNA from testing patient and detecting and calculating of methylation (or demethylation) proportion of GFRa1 CpG islands;
d) Comparing the methylation (or demethylation) proportion determined in the step c) with the cutoff value of methylation (or demethylation) determined in the step b).
e) If the methylation (or demethylation) proportion determined in the step c) is less (or greater) than or equal to the cutoff value of methylation (or demethylation) determined in the step b), occurrence of tumor should be considered; or
If the methylation (or demethylation) proportion in step c) is greater (or less) than the cutoff value of methylation (or demethylation) determined in the step b), occurrence of tumor is not considered.

Further, the methods of detection and calculation of the GFRa1 CpG islands methylation (or demethylation) proportion in step b) and c) are as follows: chemical modifying of the unmethylated cytosine; designation and synthesis of PCR primers which can match with the methylated (or demethylated) CpG island of modified GFRa1 sequences; amplification of methylated (or demethylated) GFRa1 CpG islands using these primers; detection and calculation of the methylation (or demethylation) proportion of GFRa1 CpG islands using quantitative methylation assays. Other methods in the art can also be used to analyze the GFRa1 methylation level, such as sequencing based on methylated DNA enrichment and the combination with other technologies.

Further, the cutoff value of methylation (or demethylation) proportion of GFRa1 CpG islands is determined through the method of ROC curve in step b).

The invention further involves the modified DNA sequences of GFRa1 CpG islands mentioned in step b) and step c) are shown in SEQ ID NO.1, SEQ ID NO.2, SEQ ID NO.3, and SEQ ID NO.4.

Further more, the GFRa1 methylation (or demethylation) proportion in step b) and step c) is quantified with DHPLC, bisulfite-sequencing, or probe-based, quantitative, methylation-specific PCR (MethyLight).

Preferably, the primer sets in the quantitative methylation analysis used DHPLC or bisulfite-sequencing are:
a) The primer set whose base sequences are showed in SEQ ID NO.5 and SEQ ID NO.6; or
b) The primer set whose base sequences are showed in SEQ ID NO.7 and SEQ ID NO.8.

Preferably, the primer sets and probes in the MethyLight analysis are:
a) The oligonucleotide group that is made up of the primer set whose base sequences are showed in SEQ ID NO.9 and SEQ ID NO.10, and the probe whose base sequence is showed in SEQ ID NO.11. or
b) The oligonucleotide group which is made up the primer set whose base sequences are showed in SEQ ID NO.12 and SEQ ID NO.13, and the probe whose base sequence is showed in SEQ ID NO.14.

Further, the tumors mentioned in this invention are selected from colon cancer, gastric cancer or liver cancer.

This invention also provides a method of in vitro detection assay for risk of metastasis of cancer and postoperative survival time method including the following steps:
a) Extraction of DNA from the tumor tissues of patients with metastatic cancer and the tumor tissues of patients with non-metastatic cancer;
b) Detection and calculation of methylation (or demethylation) proportion of GFRa1 CpG islands and determination of the cutoff value for prediction of cancer metastasis.
c) Extraction of tumor DNA of testing cancer patient, detection and calculation of methylation (or demethylation) proportion of GFRa1 CpG island in the tumor tissue.
d) Comparison between the GFRa1 methylation (or demethylation) proportion determined in the step c) and the methylation (or demethylation) cutoff value determined in the step b).
e) If the methylation (or demethylation) proportion determined in the step c) is less (or greater) than or equal to the cutoff value determined in the step b), it will be estimated that the patient has a high risk of tumor metastasis and a short postoperative survival; or
If the methylation (or demethylation) proportion determined in the step c) is greater (or less) than the cutoff value determined in the step b), it will be estimated that the patient has low risk of tumor metastasis and a long postoperative survival. On the contrary, it will be estimated that the patient has a high risk of tumor metastasis and a short postoperative survival.

Further, the method of detecting and calculating the methylation (or demethylation) proportion determined in the step b) and the step c) is as follows: chemical modification of the unmethylated cytosine; designation and synthesis of PCR primers which can match with the methylated (or demethylated) CpG island of modified GFRa1 sequences; amplification of methylated (or demethylated) GFRa1 CpG islands using these primers; detection and calculation of the methylation (or demethylation) proportion of GFRa1 CpG islands using quantitative methylation assays. Other methods can also be used to analyze the GFRa1 methylation level, such as sequencing based on methylated DNA enrichment and the combination with other technologies.

Further, the cutoff value of methylated (or demethylated) GFRa1 proportion calculated in the step b) is determined through the method of ROC curve.

Further, the oligo sequence of the modified sequence of GFRa1 CpG island in step b) and c) is as shown in SEQ ID NO.1, SEQ ID NO.2, SEQ ID NO.3 or SEQ ID NO.4.

Further, quantitative analysis of GFRa1 methylation content in the steps b) and c) is carried out with DHPLC, bisulfite-sequencing, and MethyLight (probe-based, quantitative, methylation-specific PCR).

Further, in the quantitative analysis of methylation in the DHPLC and bisulfite-sequencing assay, the primer set mentioned in this invention is:
a) The primer set that is made up of oligonucleotides whose base sequence is as shown in SEQ ID NO.5 and SEQ ID NO.6; or
b) The primer set that is made up of oligonucleotides whose base sequence is as shown in SEQ ID NO.7 and SEQ ID NO.8.

Further, in the method of quantitative analysis of methylation in MethyLight assay, the oligonucleotide group mentioned in this invention is:
a) The oligonucleotide group that is made up of primer set whose base sequence is as shown in SEQ ID NO.9 and SEQ ID NO.10; and the probe whose base sequence is as shown in SEQ ID NO.11; or
b) The oligonucleotide group which is made up of primer set whose base sequence is as shown in SEQ ID NO.12 and SEQ ID NO.13, and the probe whose base sequence is as shown in SEQ ID NO.14.

Further, the tumor mentioned in this invention refers to stomach, colon or liver cancers.

This invention also provides a kind of DNA molecule whose base sequence is as showed in SEQ ID NO.1, SEQ ID NO.2, SEQ ID NO.3 or SEQ ID NO. 4.

This invention also provides a kind of primer set, whose base sequence is as showed in SEQ ID NO.5 and SEQ ID NO.6.

This invention also provides another kind of primer set, whose base sequence is as showed in SEQ ID NO.7 and SEQ ID NO.8.

This invention also provides a kind of oligonucleotide group, which includes primer set whose base sequence is as showed in SEQ ID NO.9 and SEQ ID NO.10 and the probe whose base sequence is as showed in SEQ ID NO.11.

This invention also provides a kind of oligonucleotide group, which includes primer set whose base sequence is as showed in SEQ ID NO.12 and SEQ ID NO.13, and the probe whose base sequence is as showed in SEQ ID NO.14.

This invention also provides a method to detect abnormal reactivation of GFRa1 expression. The feature of the method is: analysis of full demethylation of CpG sites around the transcription start site of GFRa1 gene. This is first recognized in the world by the inventors of the invention. Further, the invention provides a set of assays to detect abnormal reactivation of GFRa1 for determination of occurrence and metastasis of cancers and patient's postoperative survival.

In order to achieve the goals above, these methods are put forwarded based on the following research results.

Hypothesis

The occurrence and progression of tumor is a multi-factor, multi-pathway and multi-stage process. Epigenetic signatures and biological features of cancer cells may be pathway-dependent, which will lead to different prognosis. For example, the prognosis of colorectal cancer with microsatellite instability-high (MSI-H, related to inactivation of mismatch-repair genes such as MLH1) is better than those with MSI-low; prognosis of gliomas with DNA repair gene MGMT inactivation by methylation is better than those without MGMT methylation. There is a CpG island around the transcription start site of GFRa1 gene. GFRa1 is inactivated by methylation in most normal adult tissues. However its expression is obviously upregulated in many cancers. GFRa1 promotes the occurrence and progression of cancers. The inventors have firstly found that GFRa1 is demethylated in cancer tissues and the demethylation subsequently leads to upregulation of GFRa1 in cancers. According to these, the inventors hypothesize that detection of methylated (or demethylated) GFRa1 content could be used to determine occurrence of cancer, to predict metastasis of cancers and patients' survival. This hypothesis has been validated in many cancers as described below.

Validation

1. Clue:

Our genome-wide DNA methylome data shows that methylation signal ratio [gastric cancer (GC) vs. surgical margin (SM)] of GFRa1 promoter detected with microarray probes is significantly lower in the metastatic GCs than the non-metastatic GCs (FIG. 1). This suggests that GFRa1 reactivation by DNA demethylation may be a potential tumor biomarker. Therefore, following experiments are carried out to confirm this hypothesis in details.

2. Establishment of Methods to Quantitatively Detect GFRa1 Methylation and Demethylation:

the unmethylated cytosine residues in genomic DNA samples are converted to uracil residues with sodium bisulfite. A CpG-free primer set is used to amplify both the methylated and unmethylated target DNA fragments (522 bp) of GFRa1 CpG islands. Denaturing high-performance liquid chromatography (DHPLC) is used to separate and quantify the amounts of methylated and unmethylated GFRa1 molecules in the PCR products (FIG. 2). Results of bisulfite clone sequencing, a semi-quantitative assay, are consistent with DHPLC analysis (FIG. 3). These indicate that DHPLC assay could be used to quantitative analysis of ratio of methylated to unmethylated GFRa1 alleles. In order to detect GFRa1 methylation in DNA samples from the paraffin-embedded tissues, in which high-molecule DNA are broken into small-molecule DNA, a probe-based, quantitative, methylation-specific PCR assay (MethyLight) is setup to determine the methylation level in a 158 bp fragment within the core CpG island of the gene. After normalized for input DNA using the CpG-free region in reference gene COL2A1 (Widschwendter et al. Cancer Res 2004, 64:3807-3813), results of the MethyLight analysis are highly consistent with DHPLC analysis ($r=0.5$; $P=0.000$; FIG. 4). Similar association between GFRa1 methylation and cancer characteristics could be observed in both DHPLC and MethyLight analysis.

3. Reactivation of GFRa1 Expression by Demethylation of CpG Islands:

In cell lines and tissue samples with different GFRa1 methylation states, the mRNA level of GFRa1 gene is analyzed with a fluorescence-probe based, quantitative RT-PCR. Results shows that GFRa1 mRNA is detected in 4 GFRa1 demethylation positive cell lines, but not in 15 demethylation negative cell lines ($P<0.001$; FIG. 5A). Similarly, it is observed that GFRa1 mRNA levels are inversely correlated with GFRa1 methylation levels in gastric tissue samples ($P=0.041$; FIG. 5B). The same phenomenon is also observed in the colon tissues. To sum up, these results indicate that promoter DNA demethylation may reactivate GFRa1 expression.

4. GFRa1 Demethylation in Gastric Tissues is a Potential Biomarker for Screen of Gastric Cancer:

GFRa1 demethylation levels in normal/gastritis biopsies from 48 non-cancer control patients (10 normal and 38 chronic gastritis), 98 gastric cancers and the corresponding surgical margin "normal" tissue samples are analyzed by using of DHPLC. The results show that the methylated: demethylated GFRa1 ratio in the normal/gastritis biopsies (Median, 60.4%) is significantly higher than that in GCs (51.0%, $P=0.043$) or SM samples (14.5%; $P<0.01$). It indicates that GFRa1 is demethylated in the development of gastric cancer and that the demethylation occurs both in gastric cancer tissues and adjacent non-cancerous tissues as a field effect. Therefore, it is very useful for screening of gastric cancer at early stage using gastric biopsies, in which cancer cells may not be sampled in some cases.

To investigate the feasibility of screening of gastric carcinomas using GFRa1 as a biomarker, the cutoff value of GFRa1 methylation: demethylation ratio is calculated using the receiver operating characteristic curve (ROC). The area under the ROC is 67.3% ($P<0.001$, FIG. 6B), according to above GFRa1 methylation results for gastric cancer and non-cancer patients. When the cutoff value is set at 22.8% ($\leq 22.8\%$ for demethylation positive and $>22.8\%$ for demethylation negative), the demethylation positive rate in normal/gastritis samples (15/48=31.2%) is much lower than the surgical margin (77/98=78.5%) and gastric cancer tissues (60/98=61.2%) ($P<0.001$). Sensitivity and specificity of GFRa1 demethylation positive in surgical margin tissue for screening of gastric cancer is 79% and 69%, respectively.

5. GFRa1 Demethylation is a Potential Biomarker for Prediction Metastasis of Gastric Carcinomas and Patients' Overall Survival:

In analysis of relationship between GFRa1 demethylation and gastric cancer metastasis or patients' overall survival, it is found that the proportion of methylated-GFRa1 in 49 non-metastatic gastric carcinomas is significantly higher than that in 49 metastatic carcinomas (Median, 60.6% vs. 22.8%, $P=0.044$). Therefore, the metastasis status of gastric carcinoma is used as a golden standard to calculate the ROC curve to evaluate the efficiency to use GFRa1 methylation as a classifier for prediction of cancer metastasis. It is found the area under the ROC curve (AUC) is 65.6% ($P=0.004$; FIG. 7). When the cutoff value of the proportion of methylated-GFRa1 is set at 16.4% ($\leq 16.4\%$ for GFRa1 demethylation-high and $>16.4\%$ for the demethylation-low), the demethylation-high rate in metastatic gastric carcinomas 71% (35/49) is significantly higher than in non-metastatic gastric carcinomas 49% (24/49; $P=0.038$) (sensitivity of 71% and specificity of 51%). Kaplan-Meier analysis shows that GFRa1 demethylation-high patients' overall survival is shorter than the demethylation-low patients (5-year survival rate, 32.8% vs. 62.2%; log-rank test, $P=0.001$; multivariate analysis, $P=0.002$; FIG. 8).

Above findings are further validated among 120 independent patients with gastric carcinomas without distant metastasis. Again, it is found that the proportion of methylated-GFRa1 in 47 non-metastatic cancer tissues is significantly higher than that in 73 lymphonodus metastatic cases (Median, 49.0% vs. 30.6%, $P<0.001$). Using the same cutoff value (16.4%), GFRa1 demethylation-high rate in the metastatic cases (46/73) is significantly higher than that in non-metastatic cases (19/47) (63.1% vs. 40.4%, P=0.024; sensitivity of 63% and specificity of 60%). Kaplan-Meier analysis also shows that the demethylation-high patients have a significant shorter overall survival than demethylation-low patients (5-year survival rate, 47.7% vs. 71.7%; log-rank test, P=0.015; multivariate analysis, P=0.025; FIG. 9). Results in the discovery and validation studies show that demethylation levels of GFRa1 CpG islands in gastric carcinomas are closely correlated with cancer metastasis and overall survival of patients. These results indicate GFRa1 demethylation may be a useful biomarker for prediction of cancer metastasis.

6. GFRa1 Demethylation is a Biomarker to Predict Occurrence and Metastasis of Colon Cancer and Patients' Survival.

In order to study relationship between GFRa1 demethylation and prognosis of other cancers, GFRa1 demethylation levels in colon mucosal biopsy samples from 21 non-cancer patients, 97 colon cancers and their corresponding surgical margin tissues are analyzed with the DHPLC assay. The results show that the proportion of methylated-GFRa1 in the colon biopsies (Median, 64.1%) is significantly higher than in colon carcinomas (31.6%; P=0.001) and the surgical margin tissues (26.6%; P<0.001; FIG. 10). The area under the ROC curve is 74.1% according to results of the methylation analysis using cancer tissues and control biopsies from non-cancer patients (P<0.001; FIG. 11). When the cutoff value is set at 34.5% (≤34.5% for demethylation positive and >34.5% for demethylation negative), GFRa1 demethylation positive rate in 7/21 control biopsies from non-cancer patients (33.3%) is significantly lower than that in 93/97 surgical margin sample (95.8%; P<0.001) and 60/97 cancer samples (61.9%; P<0.001). Using GFRa1 demethylation positive in the non-cancer biopsies or surgical margin samples as a biomarker for screening of colon cancer, the sensitivity and specificity is 95.8% and 66.7%, respectively.

Furthermore, relationship between GFRa1 demethylation and colon cancer metastasis is also analyzed among these 97 colon cancer patients (49 non-metastatic and 48 metastatic cancers). The proportion of methylated-GFRa1 in 49 non-metastasis cases is significantly higher than that in 48 metastasis cases (Median, 45.6% vs. 25.0%, P=0.016). The area under the ROC curve (AUC) is 62.6% (P=0.033; FIG. 12). When the cutoff value is set at 27.6% (≤27.6% for GFRa1 demethylation-high and >27.6% for the demethylation-low), the GFRa1 demethylation-high positive rate in 48 metastatic cancers (33/48=68.8%) is significant higher than in 49 non-metastasis cancers (22/49=44.9%; P=0.024; sensitivity of 69% and specificity of 55%). Kaplan-Meier analysis showed that GFRa1 demethylation-high cancer patients had a significant shorter overall survival than demethylation-low patients (3-year survival rate, 41.8% vs. 66.7%; log-rank test, P=0.019; multivariate analysis, P=0.031; FIG. 13).

Similar results are observed when the methylation-specific fluorescence quantitative PCR is used to detect the GFRa1 demethylation level in these tissues. The area under the ROC curve (AUC) is 61.7% (P<0.05; FIG. 14). When the cutoff value is set at 22.3% (≤22.3% for GFRa1 demethylation-high and >22.3% for the demethylation-low), the GFRa1 demethylation-high positive rate in 48 metastatic cancers (40/48) is significant higher than in 49 non-metastasis cancers (31/49) (83.3% vs. 63.3%, P=0.038; sensitivity of 83% and specificity of 37%). Kaplan-Meier analysis shows that GFRa1 demethylation-high cancer patients have a significant shorter overall survival than demethylation-low patients (3-year survival rate, 46.5% vs. 69.2%; FIG. 15).

7. GFRa1 Demethylation is a Biomarker to Predict Occurrence and Metastasis of Other Cancers and Patients' Survival.

Relationship between GFRa1 demethylation and prognosis of hepatocellular carcinomas (HCCs) is also analyzed. Results shows that the proportion of methylated GFRa1 alleles in 20 non-metastatic HCCs is higher than that in 17 metastatic HCCs (Median, 55.6% vs 41.4%, P=0.065). The area under the ROC curve (AUC) is 68.4% (FIG. 16). When the cutoff value is set at 49.3% (≤49.3% for GFRa1 demethylation-high and >49.3% for the demethylation-low), GFRa1 demethylation-high positive rate in 17 metastatic HCCs (12/17) is significantly higher than in 20 non-metastatic HCCs (11/20) (70.5% vs. 55%, P=0.024; sensitivity of 70% and specificity of 45%). Kaplan-Meier analysis also shows that the GFRa1 demethylation-high patients have a shorter overall survival than the GFRa1 demethylation-low patients (FIG. 17).

In addition, it is found that GFRa1 CpG islands are completely demethylated in lung cancer cell A549 and prostate cancer cells PC-3. The results described above indicate that GFRa1 demethylation is associated with occurrence of multiple cancers.

To sum up, the present data shows that demethylation of GFRa1 CpG islands is a potential biomarker for screening of various cancers and high level of GFRa1 demethylation can be used to predict metastasis of multiple cancers and patients' overall survival time.

BRIEF DESCRIPTION OF DRAWINGS

FIG. 1A is locations of the 522 bp amplicon (the black thick lines) and microarray probes for detection of methylation (the black squares) for GFRa1 CpG island. FIG. 1B is comparison of intensity of DNA methylation signal at different sectors of GFRa1 CpG islands in the DNA methylome database. Differential methylation in the promoter region is observed between metastatic gastric carcinoma (M+) and non-metastatic gastric cancer (M−).

FIG. 2A refers to result of demethylated GFRa1 of human cell lines; FIG. 2B is for gastric tissue; Genomic DNA of peripheral white blood cells is used as the negative control; M.sssI-methylated blood DNA is used as the positive control.

FIG. 5A is correlation analysis using 19 human cell lines; FIG. 5B is correlation analysis using gastric carcinomas and the surgical margin tissues.

FIG. 6A shows percentages of methylated GFRa1 in gastric tissues at different pathological states; FIG. 6B shows the cutoff value of ROC curve of detection of gastric carcinoma using GFRa1 methylation content in the gastric tissues from cancer and non-cancer patients.

Figure 1:
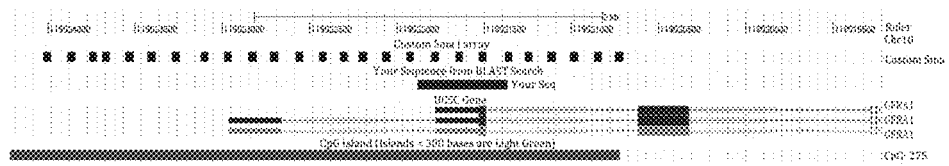
FIG. 1 refers to comparison of intensity of DNA methylation signal at different sectors in GFRa1 CpG islands in the database of DNA methylome of gastric carcinomas and the surgical margin tissues.

Next, the detailed illustration of the invention will be made through living example. If it is not pointed out, the materials, methods and equipment are all the regular materials, methods and equipment in this area.

BEST EMBODIMENTS

Example 1

Screening for Gastric Cancer Through Detection of Demethylation of GFRa1 CpG Islands in Gastric Tissue by Using of DHPLC 1. Subjects: gastric mucosa biopsies from 48 non-cancer patients (10 cases without observed pathological changes in the stomach and 38 cases with chronic gastritis), gastric carcinomas and the paired surgical margin frozen tissue samples from 98 patients;

2. Regularly digest tissue protein using proteinase K and then extracting genomic DNA (about 10 μg) using the regular ethanol precipitation method.

3. Modifying the unmethylated cytosine residues in DNA samples using 5M sodium bisulfite, including following steps;
   1) Adding and dissolving 2 μg genomic DNA prepared in the step 2 into 18 μl of distilled sterile water, incubating the tube in water bath at 95° C. for 20 min, and then incubating in the ice bath.
   2) Adding 2 μl of 3M NaOH, mixing and incubating at 42° C. for 20 min to denature double strands DNA.
   3) Preparing for 5M sodium bisulfite solution (NaHSO$_3$, 4 ml): adding 1.9 g of Na$_2$S$_2$O$_5$ into 2.5 ml distilled sterile water, adding 0.7 ml of 2M NaOH solution and 0.5 ml of 1M hydroquinone, incubating in a water bath at 50° C., with repeatedly inverting and mixing until completely dissolved.
   4) Adding 380 μl of fresh 5M NaHSO$_3$ solution and mixing. Covering the top of reaction with 200 μl of liquid paraffin to prevent evaporation of reaction. Incubating in the water bath at 50° C. overnight to convert the unmethylated cytosine residues to uracil residues.
   5) Removing |[s1] liquid paraffin. Purifying the modified DNA with Wizard DNA Clean-Up System (Promega A7280) as the kit instruction: adding 1 ml of the mixture of resin and staying for 5 minutes after mixing; transferring the resin-DNA mixture into an injector tube connected to a micro-column filter; removing liquid phase and transferring the DNA sample onto solid phase in the micro-column filter through vacuum; adding 2 ml of 80% isopropyl alcohol, removing the liquid within the injector-filter through vacuum, and disconnecting the injector tube; setting the micro-column filter into another centrifuge tube (1.5 ml), centrifuging at high-speed (10,000 g, 20 seconds) to remove residual liquid in the column filter; setting the micro-column filter to another centrifuge tube.
   6) Adding 50 μl of distilled sterile water (pre-warmed at 80° C.) into the micro-column, standing for 15 min, centrifuging at high-speed (10,000 g, 20 seconds) to collect the eluent. Repeating this washing process again. Pooling the eluent solution.
   7) Adding 11 μl of 3M NaOH solution, mixing and incubating in the water bath at 37° C. for 15 min to terminate further modification.
   8) Adding 166 μl of 5M NaOAC and 750 μl of 100% cold ethanol, mixing and storing at −20° C. for 4 hours to precipitate the DNA. Centrifuging at 10,000 g for 30 min and discarding the solution. Adding 200 μl of 80% cold ethanol to wash the DNA. Centrifuging again and discarding the solution.
   9) Resuspending the DNA in 3-6 μl of sterile water or TE buffer. Using immediately or storing at −20° C.

4. Design of PCR primer sets. According to the modified GFRa1 sense-strand sequence (SEQ ID NO:1 and SEQ ID NO:2), designing and synthesizing CpG-free universal primer sets (SEQ ID NO:5; the SEQ ID NO:6 or SEQ ID NO:7; the SEQ ID NO:8).

5. PCR amplification. Both the methylated and demethylated fragments (522 bp or 463 bp) in GFRa1 alleles in the modified DNA sample are amplified by using a hot start PCR.

6. Detection of the methylated and demethylated GFRa1 CpG islands in the PCR product by using of DHPLC. Calculating the peak-area proportion for the demethylated GFRa1:

the percentage of demethylated GRFa1=[the peak area for demethylated GFRa1]/[total peak areas for both demethylated and methylated GFRa1 PCR products]×100%;

or calculating the methylated GFRa1:

the percentage of methylated GRFa1=[the peak area for methylated GFRa1]/[total peak areas for both demethylated and methylated GFRa1 PCR products]×100%, or, the percentage of methylated GRFa1=1−(the peak area proportion for demethylated GFRa1).

Figure 2:
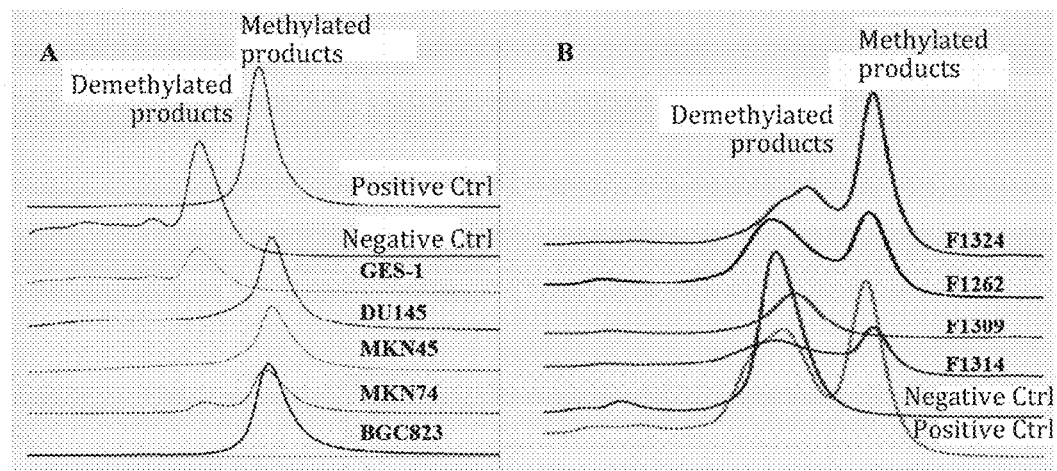
FIG. 2 is chromatograms of 522 bp amplicon of methylated and demethylated GFRa1 CpG islands in the bisulfite-DHPLC analysis.
Figure 3:
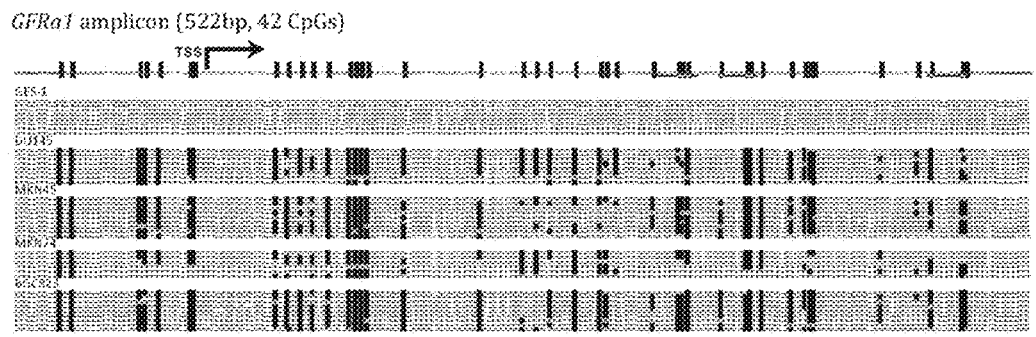
FIG. 3 is results of bisulfite-sequencing of the 522 bp PCR clones from GFRa1 CpG islands in human cell lines. The strong black dots represent methylated CpG sites; GFRa1 is fully methylated in Du145, MKN45 and BGC823 cells, partly methylated in MKN74 cell, and demethylated in GES-1 cell.
Figure 4:
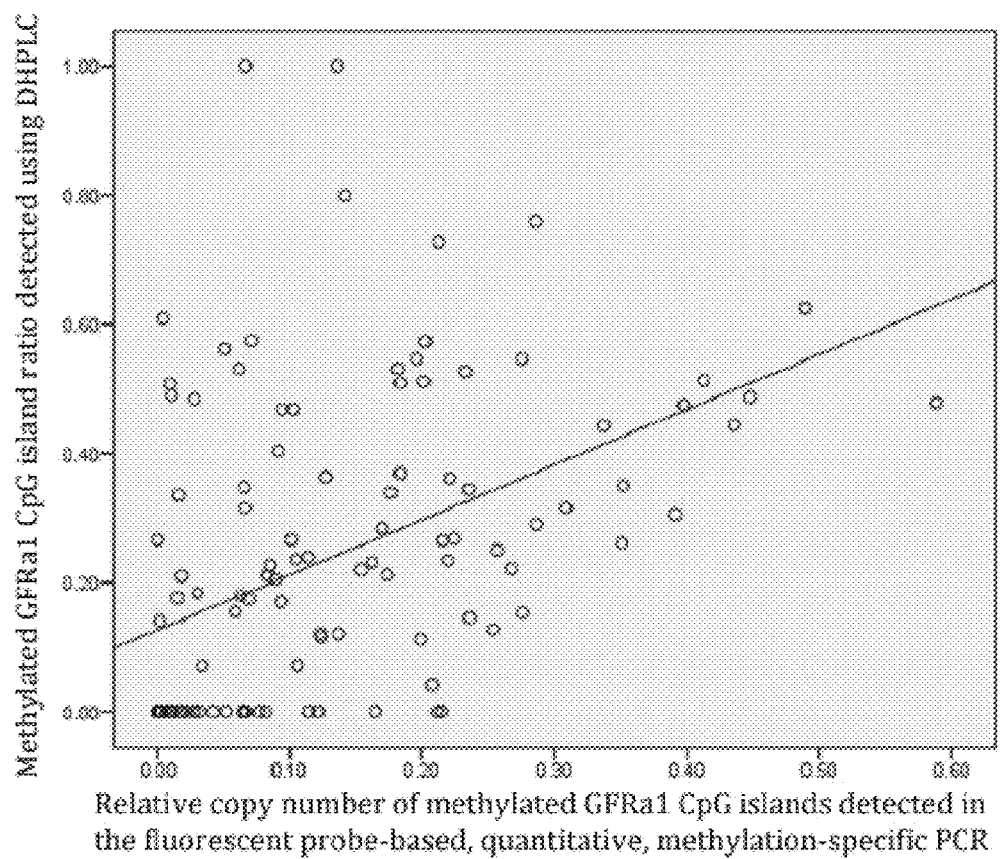
FIG. 4 is the correlation analysis of GFRa1 methylation levels detected with DHPLC and fluorescence-probe-based, quantitative, methylation-specific PCR (MethyLight) analysis.
Figure 5:
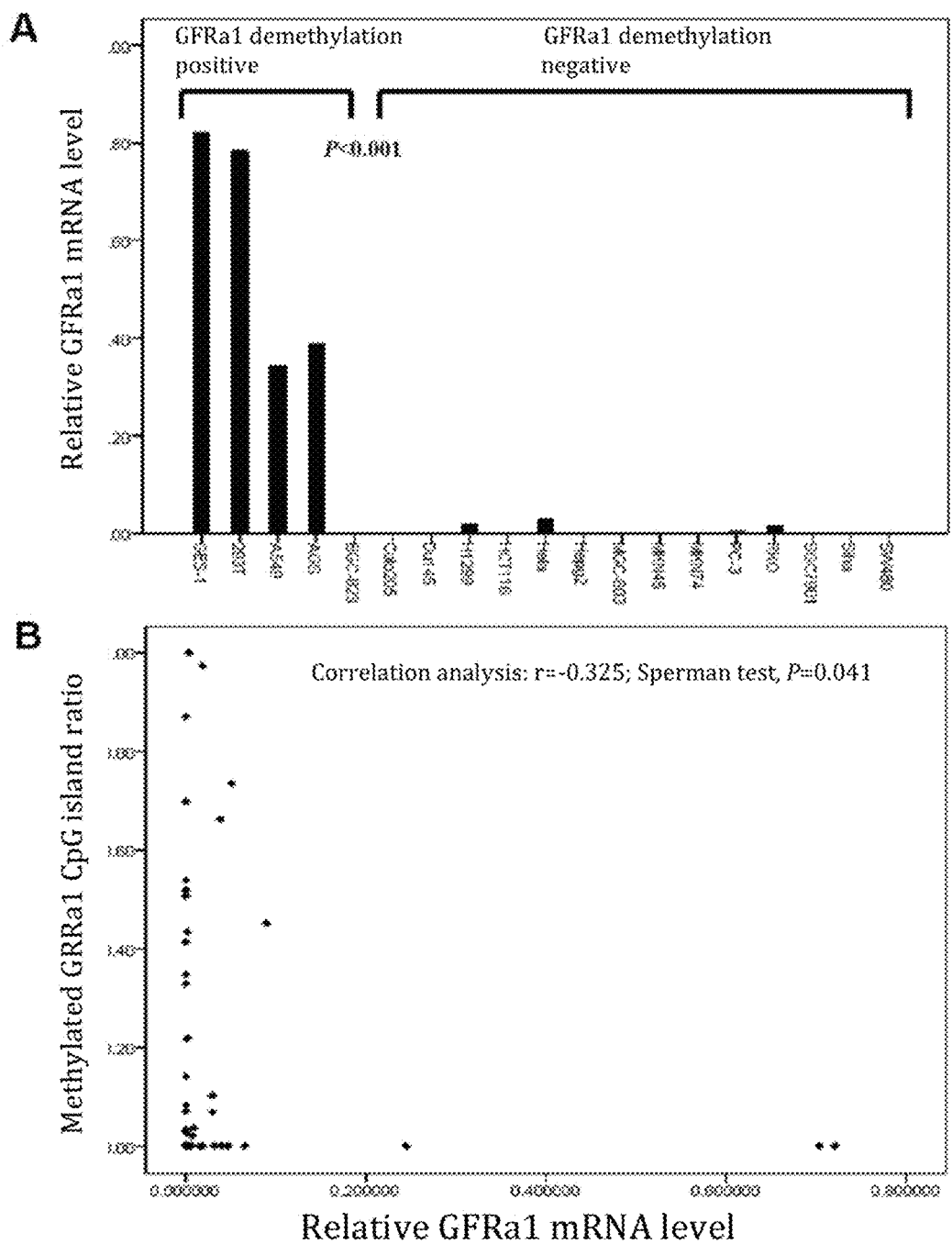
FIG. 5 shows relationship between GFRa1 demethylation and GFRa1 transcription level.
Figure 6:
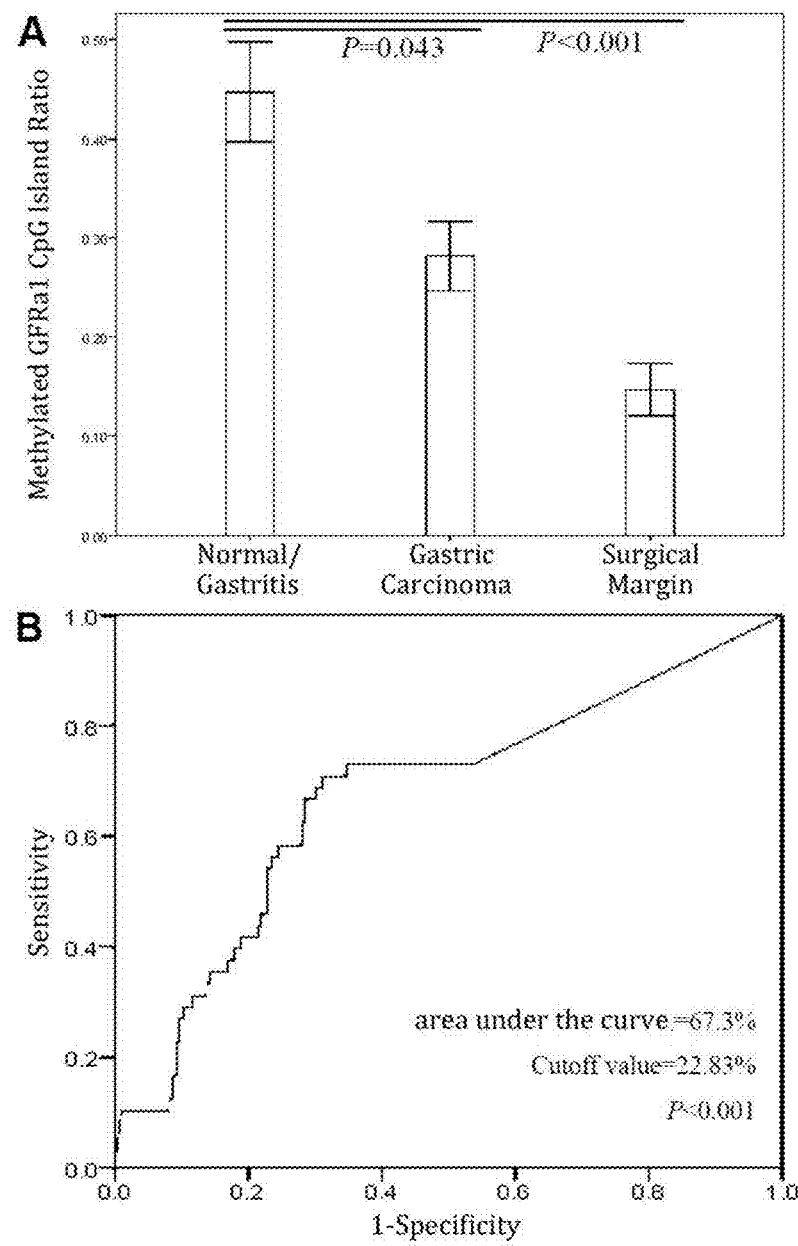
FIG. 6 indicates the comparison of GFRa1 methylation level between normal/or gastritis biopsies from non-cancer patients and gastric carcinomas and the surgical margin samples.

7. Result: The average peak-area proportion for the methylated GFRa1 in normal gastric biopsies is similar to that in gastritis biopsies and the average percentage of methylated GFRa1 in these normal/gastritis samples is 60.4% (Median), which is significantly higher than that in gastric carcinomas and the surgical margin samples (51.0%, P=0.043; and 14.5%, P=0.000; FIG. 6A), respectively. Therefore, the receiver operating characteristic curve (ROC) for screening of gastric carcinomas using GFRa1 methylation percentage as a biomarker is calculated. When the cutoff value is set at 22.8% (≤22.8% for demethylation positive and >22.8% for demethylation negative), the demethylation positive rate in normal/gastritis samples (15/48=31.2%) is much lower than the surgical margin (77/98=78.5%) and gastric cancer tissues (60/98=61.2%) (P<0.001). Sensitivity and specificity of GFRa1 demethylation positive in surgical margin tissue for screening of gastric cancer is 79% and 69%, respectively (FIG. 2B).

Example 2

Detection of Metastasis of Gastric Carcinomas and Patients' Survival Through Detection of Demethylation of GFRa1 CpG Islands by Using of DHPLC 1. Subjects: gastric carcinoma frozen-tissue samples from 98 patients (including 49 patients with gastric carcinomas with metastasis to lymph or distant sites and embolus and 49 patients with non-metastatic gastric carcinomas) in the discovery cohort. Gastric carcinoma frozen-tissue samples from 120 patients (including 73 gastric carcinomas with lymph but not distant metastasis and 47 non-metastatic gastric carcinomas) in the validation cohort. Clinicopathologic and follow-up data are available for all of these subjects.

Figure 7:
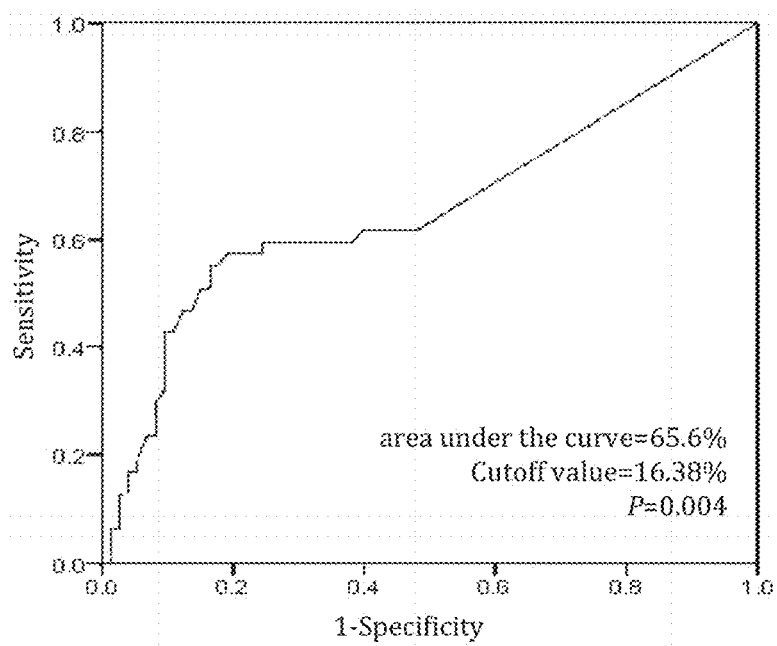
FIG. 7 is the ROC curve of detection of gastric cancer metastasis by using GFRa1 demethylation content as a classifier.
Figure 8:
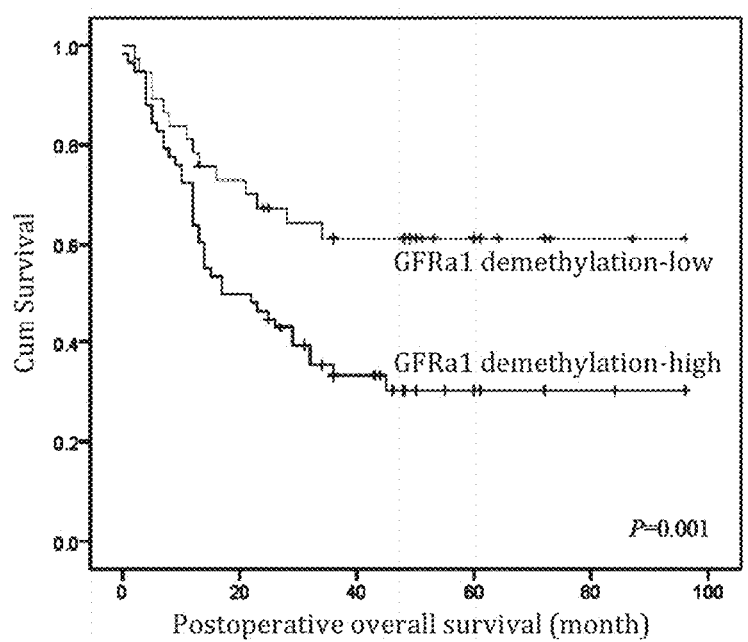
FIG. 8 shows the Kaplan-Meier curve of post-operational overall survival time of 98 GFRa1 demethylation-high or demethylation-low gastric cancer patients in the discovery cohort.

2. The same as the steps 2-5 in the Example 1;
3. The same as the step 6 in the Example 1;
4. Result:

The average peak-area proportion for the methylated GFRa1 in 49 non-metastatic gastric carcinoma samples is significantly higher than that in 49 metastatic gastric carcinoma samples (Median, 60.6% vs. 22.8%, P=0.044). According to the ROC curve for detection of gastric carcinoma metastasis using GFRa1 methylation as a classifier, the area under the ROC curve (AUC) is 65.6% (P=0.004, FIG. 7). When the cutoff value is set at 16.4% (≤16.4% for GFRa1 demethylation-high and >16.4% for the demethylation-low), the demethylation-high rate in metastatic gastric carcinomas (35/49=71%) is significantly higher than in non-metastatic gastric carcinomas (24/49=49%) (P=0.038; sensitivity of 71% and specificity of 51%). Kaplan-Meier analysis showed that GFRa1 demethylation-high patients' overall survival is shorter than the demethylation-low patients (5-year survival rate, 32.8% vs. 62.2%; log-rank test, P=0.001; multivariate analysis, P=0.002; FIG. 8).

Figure 9:
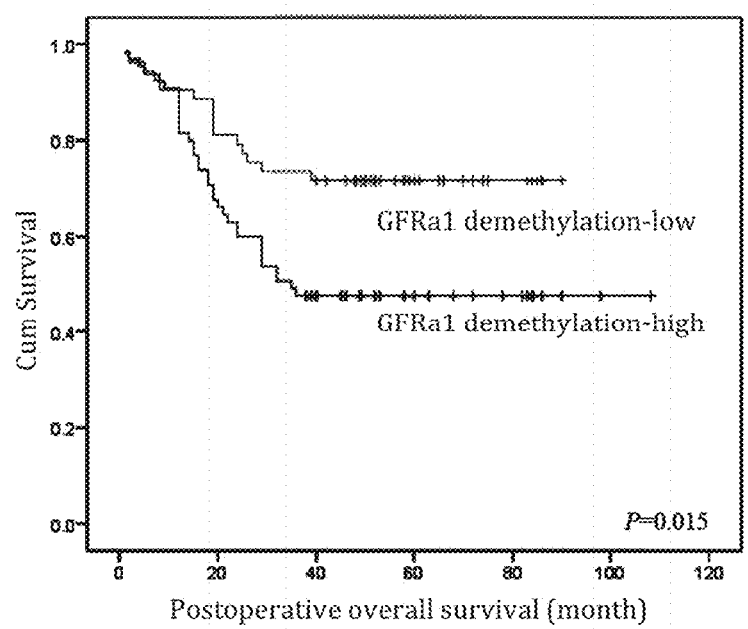
FIG. 9 shows the Kaplan-Meier curve of post-operational overall survival of 120 GFRa1 demethylation-high or demethylation-low gastric cancer patients in the validation cohort.

In the validation cohort, the average peak-area proportion for the methylated GFRa1 in 47 non-metastatic cancer tissues is significantly higher than that in 73 metastatic cases (Median, 49.0% vs. 30.6%, P<0.001). Using the same cutoff value (16.4%) used in the above discovery cohort, GFRa1 demethylation-high rate in the metastatic cases (46/73=63.1%) is significantly higher than that in non-metastatic cases (19/47=40.4%) (P=0.024; sensitivity of 63% and specificity of 60%). Kaplan-Meier analysis also shows that the demethylation-high patients have a significant shorter overall survival than demethylation-low patients (5-year survival rate, 47.7% vs. 71.7%; log-rank test, P=0.015; multivariate analysis, P=0.025; FIG. 9).

Example 3

Figure 18:
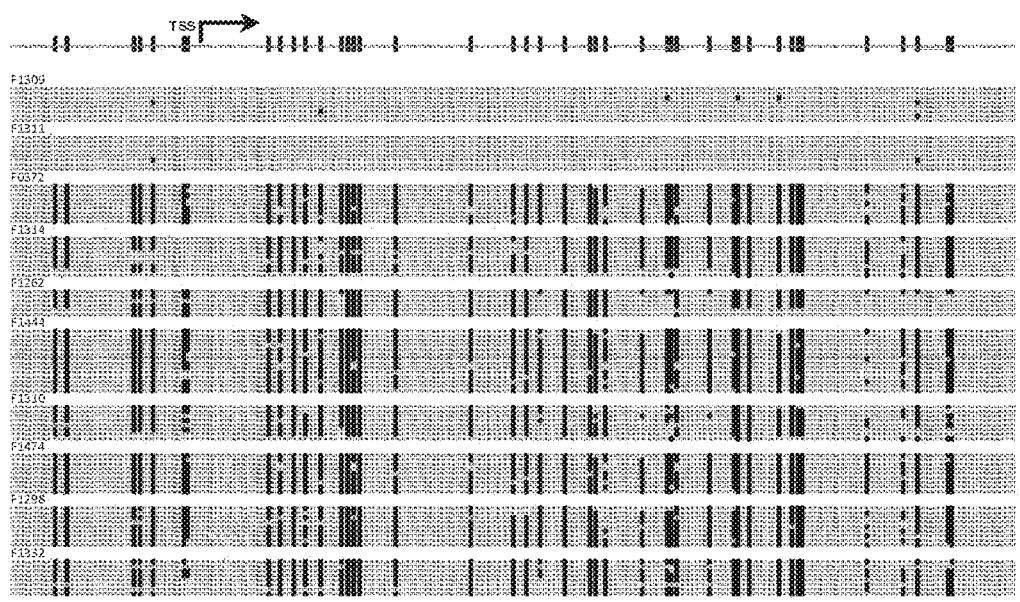
FIG. 18 is the results of bisulfite-sequencing of 522 bp PCR products of GFRa1 CpG islands in gastric tissue samples. The strong black dots represent methylated CpG sites; GFRa1 is completely demethylated in samples F1309 and F1311, but not demethylated in other representative samples.

Screening for Gastric Cancer Through Detection of Demethylation of GFRa1 CpG Islands in Gastric Tissue Using Bisulfite-Sequencing 1. The same as the steps 1-5 in the Example 1.
2. The PCR products are cloned using the AT-Clone Kit and sequenced (FIG. 18).
3. Result: the same result is achieved as the Example 1.

Example 4

Detection of Metastasis of Gastric Carcinomas and Patients' Survival Through Detection of Demethylation of GFRa1 CpG Islands Using Bisulfite-Sequencing 1. The same as the steps 1-2 in the Example 2.
2. The same as the step 2 in the Example 3.
3. Result: The same result is achieved as the Example 2.

Example-5

Figure 10:
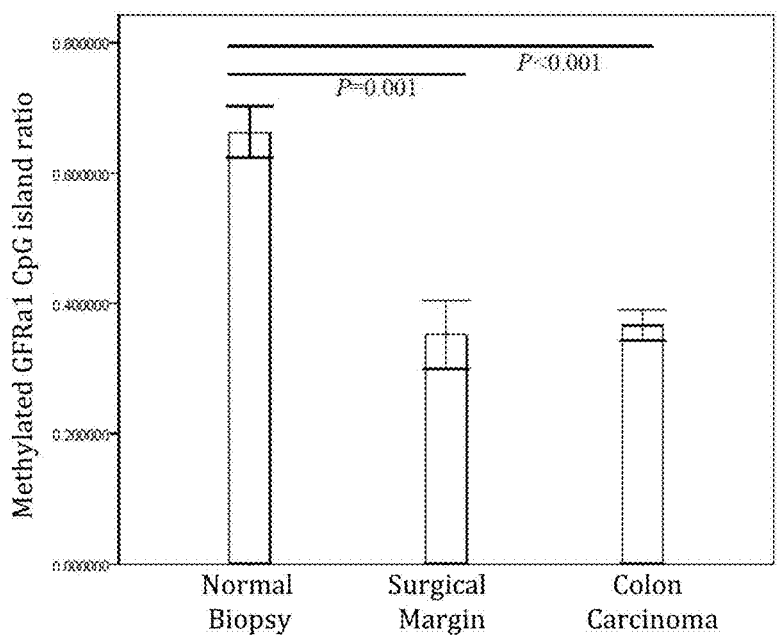
FIG. 10 is the comparison of GFRa1 methylation level between colon biopsies from non-cancer patients, colon cancer and the surgical margin samples.
Figure 11:
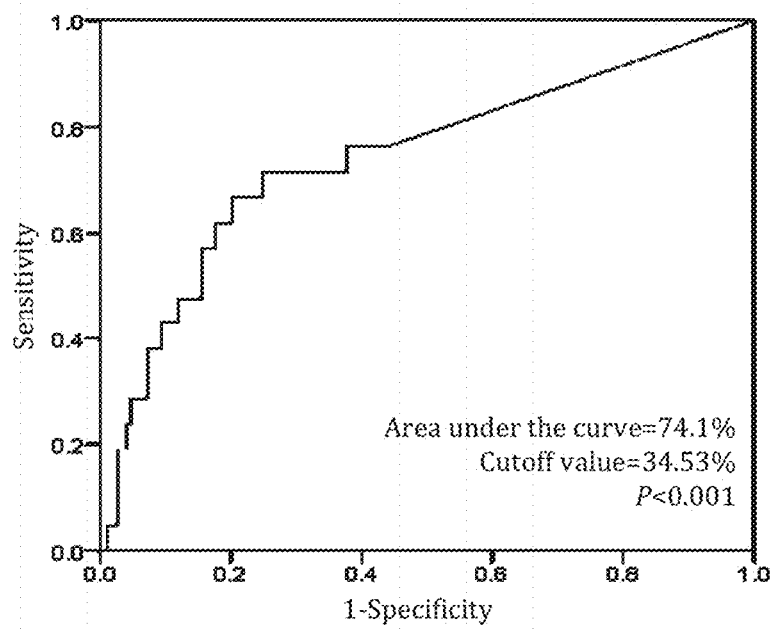
FIG. 11 is the cutoff value of ROC curve of detection of colon carcinoma using GFRa1 methylation content in colon biopsies from non-cancer patients and the surgical margin tissue samples from colon cancer patients.

Screening for Colon Cancer Through Detection of Demethylation of GFRa1 CpG Islands in Colon Tissue by Using of DHPLC 1. Subjects: colon mucosal biopsy samples from 21 non-cancer patients and colon cancer and surgical margin samples from 97 patients;
2. The same as the steps 2-6 in the Example-1.
3. Result:

The average proportion of methylated-GFRa1 in the colon biopsies from non-cancer patients (Median, 64.1%) is significantly higher than colon carcinomas (31.6%; P<0.001) and the surgical margin tissues (26.6%; P=0.001; FIG. 10). The area under the ROC curve is 74.1% according results of the methylation analysis using cancer tissues and control biopsies from non-cancer patients (P<0.001; FIG. 11). When the cutoff value is set at 34.5% (≤34.5% for demethylation positive and >34.5% for demethylation negative), GFRa1 demethylation positive rate in 21 control biopsies from non-cancer patients (7/21=33.3%) is significantly lower than that in 97 surgical margin sample (93/97=95.8%; P<0.001) and 97 cancer samples (60/97=61.9%; P<0.001). Using GFRa1 demethylation positive in the non-cancer biopsies or surgical margin samples as a biomarker for screening of colon cancer, the sensitivity and specificity is 95.8% and 66.7%, respectively.

Example 6

Figure 12:
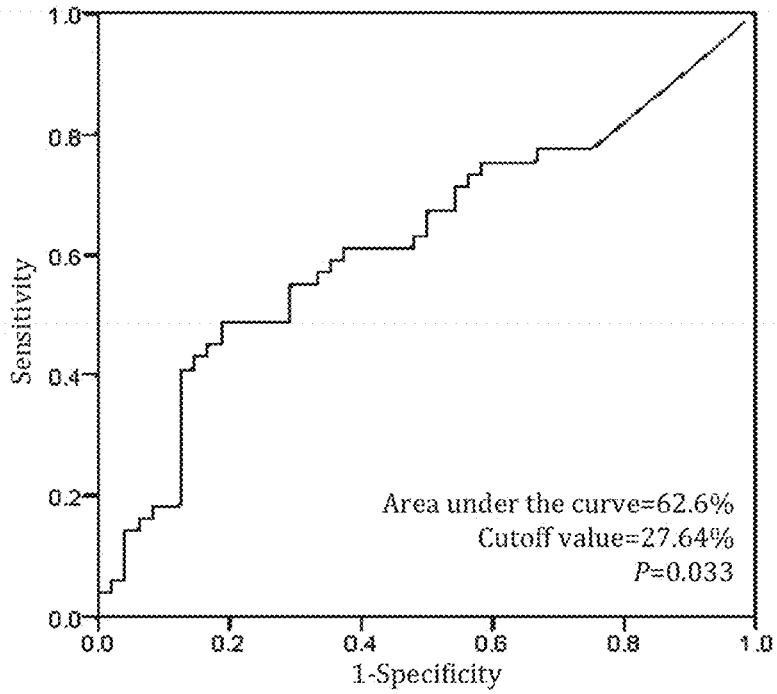
FIG. 12 is the ROC curve of detection of metastasis and non-metastasis of colon cancers using the extent of GFRa1 demethylation.
Figure 13:
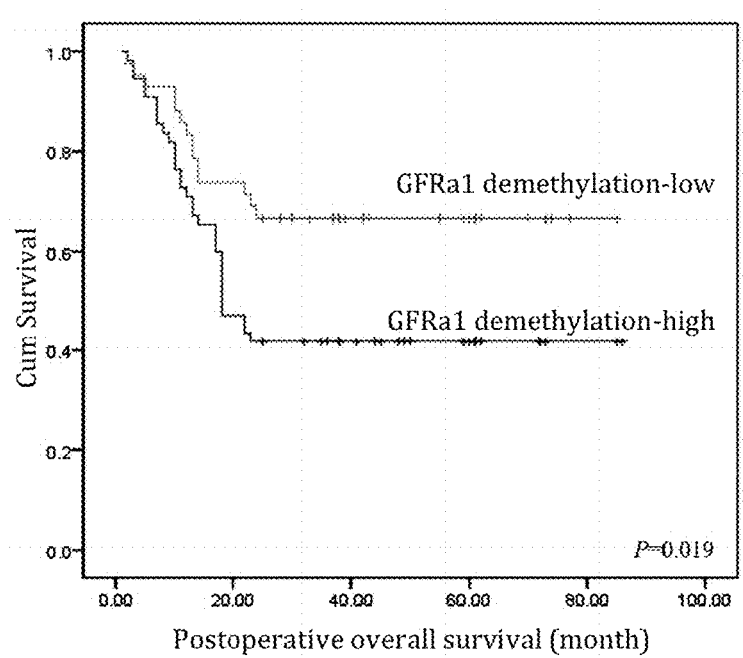
FIG. 13 is the Kaplan-Meier curve of post-operational overall survival time of 97 GFRa1 demethylation-high or demethylation-low colon cancer patients.

Detection of Metastasis of Colon Carcinomas and Patients' Survival Through Detection of Demethylation of GFRa1 CpG Islands by Using of DHPLC 1. Subjects: colon cancer tissues from 49 patients without metastasis, and metastatic colon cancer tissues from 48 control patients. Clinicopathologic and follow-up data are available for all of above subjects.
2. The same as the steps 2-6 in the Example 1.
3. Results: The average proportion of methylated-GFRa1 in 49 non-metastatic colon cancers is significantly higher than that in 48 metastatic cancers (Median, 45.6% vs. 25.0%, P=0.016). The area under the ROC curve (AUC) is 62.6% (P=0.033; FIG. 12). When the cutoff value is set at 27.6% (≤27.6% for GFRa1 demethylation-high and >27.6% for the demethylation-low), the GFRa1 demethylation-high positive rate in 48 metastatic cancers (33/48) is significant higher than in 49 non-metastasis cancers (22/49) (68.8% vs. 44.9%, P=0.024; sensitivity of 69% and specificity of 55%). Kaplan-Meier analysis showed that GFRa1 demethylation-high cancer patients have a significant shorter overall survival than demethylation-low patients (3-year survival rate, 41.8% vs. 66.7%; log-rank test, P=0.019; multivariate analysis, P=0.031; FIG. 13).

Example 7

Screening for Colon Cancer Through Detection of Demethylation of GFRa1 CpG Islands in Colon Tissue Using the Probe-Based, Quantitative, Methylation-Specific PCR (MethyLight)

1. Subjects: The same as the step 1 in the Example 5.
2. DNA sample management: The same as the steps 2-3 in the Example 1.
3. According to the bisulfite-modified GFRa1 sense-strand sequence (SEQ ID NO.1) or antisense-strand sequence (SEQ ID NO.3), designing and synthesizing forward and reverse PCR primers (SEQ ID NO.9 and SEQ ID NO.10) and sequence-specific fluorescent probe (SEQ ID NO.11) for the antisense-strand sequence, or designing and synthesizing forward and reverse PCR primers (SEQ ID NO.12, SEQ ID NO.13) and sequence-specific fluorescent probe (SEQ ID NO.14) for the sense-strand sequence.
4. Fluorescent probe-based, quantitative PCR amplification: the 158 bp bisulfite-modified template in both the methylated and demethylated GFRa1 alleles is amplified using the fluorescence quantitative PCR amplification.
5. As reported in the literature (Widschwendter et al. Cancer Res 2004, 64:3807-3813), the CpG island-free gene COL2A (but not limited to the gene), as the reference gene to normalize the amount of input bisulfite-modified DNA template, is amplified using the corresponding the primer set (SEQ ID NO.15 and SEQ ID NO.16) and the fluorescent probe (TaqMan; sequence SEQ ID NO.17; 6FAM-Col2$^{probe}$-BHQ1).
6. Calculating the proportion of methylated GFRa1 templates: based the Ct values for GFRa1 and COL2A1, the relative copy number of methylated GFRa1 is calculated using the formula $[2^{-(Ct_{GFRA1}-Ct_{COL2A})}]$.
7. Result: The average proportion of methylated GFRa1 in normal colon biopsies (median, 46.8%) is significantly higher than in colon carcinoma samples (12.6%, P<0.01) or their corresponding surgical margin tissues (0.0005%, P<0.01). The area under ROC curve (AUC) is 69.7% (P<0.05). When the cutoff value is set at 1.3% (≤1.3% for GFRa1 demethylation positive and >1.3% for the demethylation negative), the demethylation positive rate in colon biopsies from non-cancer patients (8/20=40%) is significantly lower than that in the surgical margin tissues (16/20=80%) and colon cancer tissues (97/97=100%, P<0.001). Sensitivity and specificity for detection of colon cancer using the demethylation-high was 80100% and 60%, respectively.

Example 8

Detection of Metastasis of Colon Carcinomas and Patients' Survival Through Detection of Demethylation of GFRa1 CpG Islands Using the Probe-Based, Quantitative, Methylation-Specific PCR (MethyLight)

Figure 14:
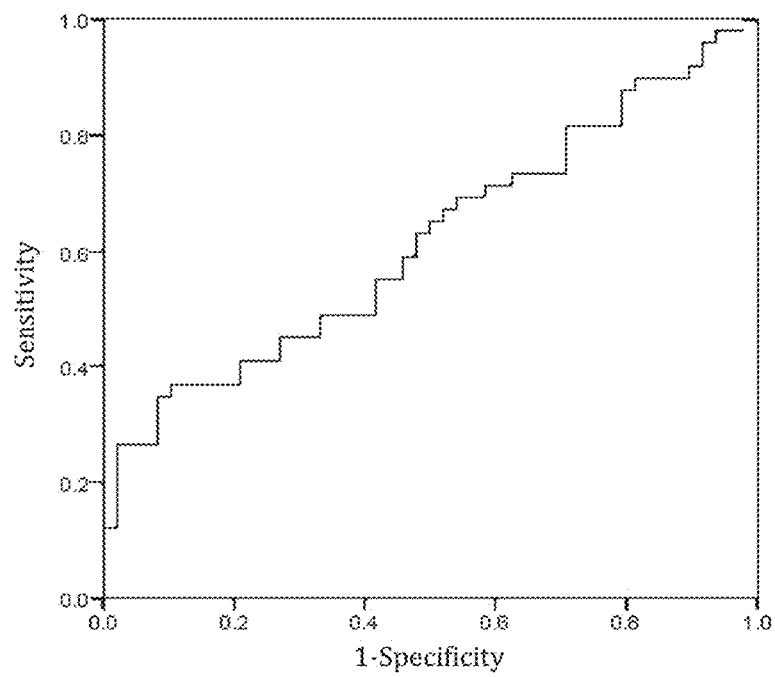
FIG. 14 is the ROC curve of detection of metastasis and non-metastasis of colon cancers using GFRa1 demethylation-high or demethylation-low, determined by using a probe-based, quantitative, methylation-specific PCR (MethyLight) assay, as a classifier.
Figure 15:
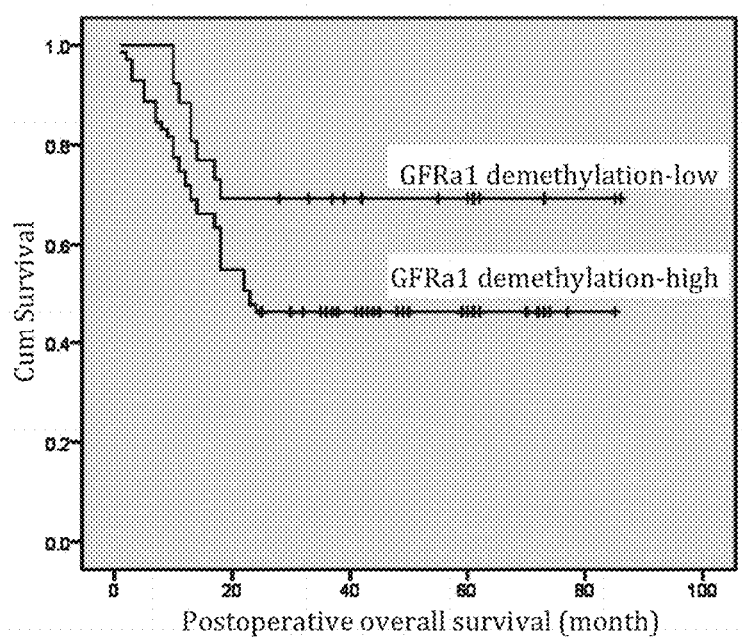
FIG. 15 is the Kaplan-Meier curve of post-operational overall survival time of 97 patients with colon cancers containing GFRa1 demethylation-high or demethylation-low in the probe-based, quantitative, methylation-specific PCR (MethyLight) analysis.

1. Subjects: The same as the step 1 in the Example 6.
2. DNA sample management and quantification of methylated GFRa1: The same as the steps 2-6 in the Example 7.
3. Setting the cutoff value. The average relative copy number of methylated GFRa1 in 49 non-metastatic colon cancers is significantly higher than that in 48 metastatic colon cancer samples (Median, 13.6% vs. 9.7%, P=0.047). The area under the ROC curve (AUC) is 61.7% (P=0.047; FIG. 14). When the cutoff value is set at 22.3% (≤22.3% for GFRa1 demethylation-high and >22.3% for the demethylation-low), the GFRa1 demethylation-high positive rate in 48 metastatic cancers (40/48) is significant higher than in 49 non-metastasis cancers (31/49) (83.3% vs. 63.3%, P=0.038; sensitivity of 83% and specificity of 37%). Kaplan-Meier analysis showed that GFRa1 demethylation-high cancer patients have a significant shorter overall survival than demethylation-low patients (3-year survival rate, 46.5% vs. 69.2%; P=0.056; FIG. 15).

Example 9

Screening for Cancers Through Detection of Demethylation of GFRa1 CpG Islands in Plasma Free DNA Using the Probe-Based, Quantitative, Methylation-Specific PCR (MethyLight)

1. Subjects: The same as the Example 1 and Example 5; 0.3 ml of anti-coagulated venous plasma from these fasting subjects is prepared.
2. According to the Blood DNA Extraction Kit (QIAGEN, Germany) Instruction Manual, free DNA sample is extracted from 0.3 ml of plasma sample from cancer and non-cancer control subjects.
3. The same as the step 3 in the Example 1.
4. The same as the steps 3-6 in the Example 7.
5. Result: The average proportion of methylated GFRa1 in the plasma free DNA sample from non-cancer control subjects is significantly higher than that from colon cancer subjects (median, 66.5% vs. 10.2%, P<0.01). The area under the ROC curve (AUC) is 79.5% (P<0.01). When the cutoff value is set at 2.3% (≤2.3% for GFRa1 demethylation positive and >2.3% for the demethylation negative), GFRa1 demethylation positive rate in the plasma samples from non-cancer subjects (4/20=20%) is significantly lower than that from colon cancer patients (97/97=100%). The sensitivity and specificity for screening of colon cancer using GFRa1 demethylation in plasma as a biomarker is 100% and 80%, respectively.

Example 10

Figure 16:
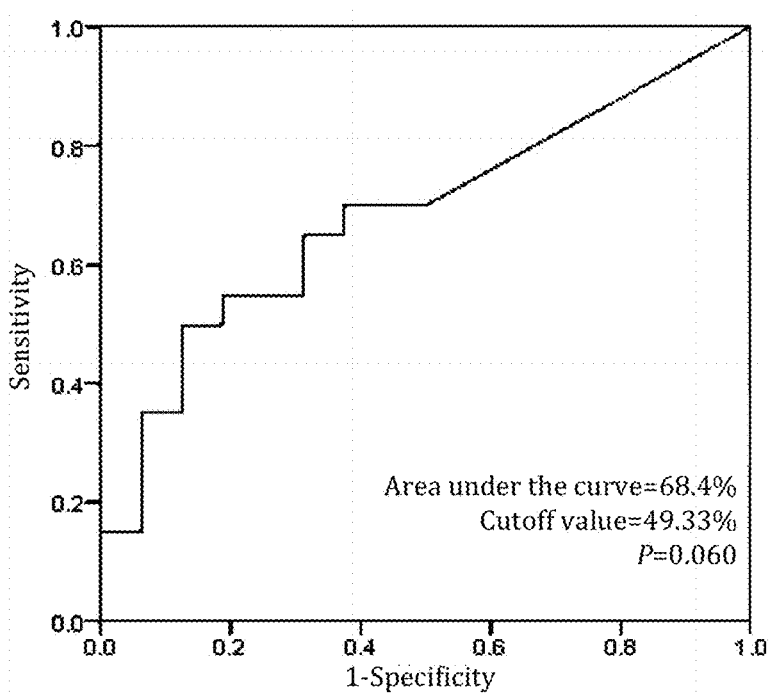
FIG. 16 is the ROC curve of detection of metastasis and non-metastasis of HCCs by using GFRa1 demethylation-high or demethylation-low.
Figure 17:
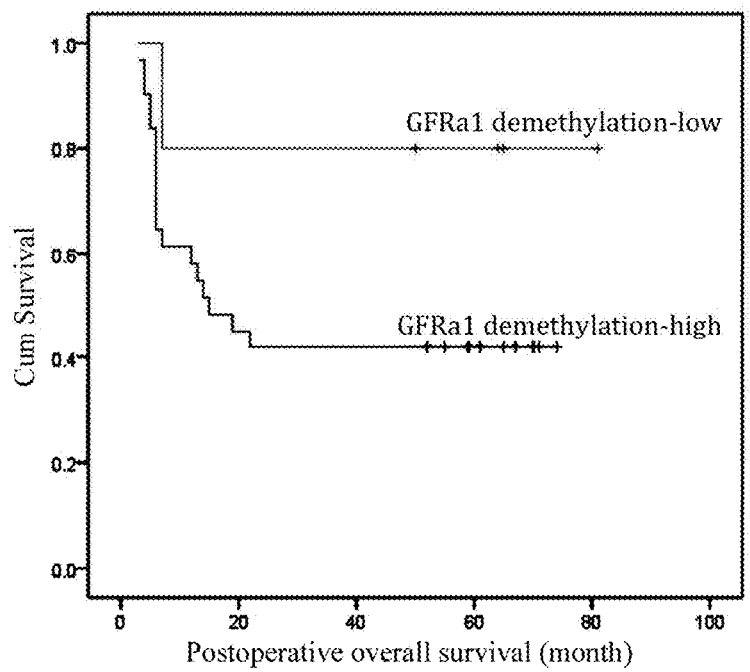
FIG. 17 is the Kaplan-Meier curve of post-operational overall survival time of 37 patients with different GFRa1 demethylationextent.

Detection of Metastasis of Hepatocellular Carcinomas and Patients' Survival Through Detection of Demethylation of GFRa1 CpG Islands by Using of DHPLC 1. Subjects: hepatocellular carcinoma samples from 37 patients, including 17 cases with metastasis/recurrence, 20 cases without metastasis/recurrence. Clinicopathologic and follow-up data are available for all of these subjects.
2. DNA management and analysis of methylated GFRa1: The same as the steps 2-6 in the Example 1.
3. Result: The average proportion of methylated GFRa1 in 20 non-metastatic hepatocellular carcinomas is significantly higher than that in 17 metastatic cases (Median, 55.6% vs. 41.4%, P=0.065). The area under the ROC curve (AUC) is 68.4% (P=0.060; FIG. 16). When the cutoff value is set at 49.3% (≤49.3% for GFRa1 demethylation-high and >49.3% for the demethylation-low), GFRa1 demethylation-high positive rate is higher in the metastatic cancers (12/17=70.5%) than non-metastatic cancers (11/20=55.0%) (P=0.067). The sensitivity and specificity of detection of liver cancer metastasis using GFRa1 demethylation-high as a biomarker is 70% and 45%, respectively. Kaplan-Meier analysis showed that patients with GFRa1 demethylation-high liver cancer have a shorter overall survival than those with GFRa1 demethylation-low liver cancers (FIG. 17).

What is claimed is:

1. A method of detection of occurrence of cancer in vitro, characterized in that said method comprises the following steps:
   a) extracting gastric, colon or liver tissue DNA or plasma free DNA from cancer and non-cancer patients;
   b) detecting and calculating the proportion of methylated or demethylated GFRa1 CpG islands in the promoter region of GFRa1 of said DNA from a): setting a cutoff value for detection of cancers using the proportion of methylated or demethylated GFRa1, wherein the cutoff value of methylated or demethylated GFRa1 is calculated by using a Receiver Operating Characteristic (ROC) curve;
   c) extracting gastric, colon or liver tissue DNA or plasma free DNA samples from testing subjects in vitro, detecting and calculating the proportion of methylated or demethylated GFRa1 CpG islands in the promoter region of GFRa1 of the DNA samples;
   d) comparing the proportion of methylated or demethylated GFRa1 CpG islands determined in the step c) with the cutoff value set in the step b); and
   e) detecting the occurrence of cancer based on the detection of a lower or equal proportion of methylated GFRa1 CpG islands determined in step c) as compared to the cutoff value set in step b), or based on the detection of a higher or equal proportion of demethylated GFRa1 CpG islands determined in step c) as compared to the cutoff value set in the step b), wherein the proportion of the methylated or demethylated GFRa1 CpGs islands is determined and calculated by DHPLC, bisulfite-sequencing or fluorescent probe-based, quantitative, methylation-specific PCR (MethyLight) using oligonucleotide groups:
   i) the primer pair set forth in SEQ ID NO: 9 and SEQ ID NO: 10, and the probe set forth in SEQ ID NO: 11; or
   ii) the primer pair set forth in SEQ ID NO: 12 and SEQ ID NO: 13, and the probe set forth in SEQ ID NO: 14, and
   wherein said cancer is gastric cancer, colon cancer or liver cancer.

2. The method of detection of occurrence of cancer in vitro according to claim 1, wherein the proportion of the methylated or demethylated CpG islands described in steps b) and c) is determined and calculated as follows: chemically modifying unmethylated cytosine so as to convert unmethylated cytosine residues in said DNA sample to uracil residues to produce modified sequences of GFRa1 CpG islands; designing and synthesizing primer sets and amplifying the methylated or demethylated GFRa1 CpG islands and determining and calculating the proportion of methylated or demethylated GFRa1 CpG islands with quantitative analysis of methylation.

3. The method of detection of occurrence of cancer in vitro according to claim 2, wherein the modified sequences of GFRa1 CpG islands are as shown in SEQ ID NO: 1, 2, 3 or 4.

4. A method of detection of metastasis of cancers and cancer patients' postoperative survival in vitro, characterized in that said method comprises the following steps:
   a) extracting gastric, colon or liver tissue DNA from patients with metastatic cancer and patients with non-metastatic cancer;
   b) detecting and calculating proportion of methylated or demethylated GFRa1 CpG islands in the promoter region of GFRa1 of said DNA from a): setting a cutoff value of demethylation-high and -low for detection of cancer metastasis using the proportion of methylated or demethylated GFRa1, wherein the cutoff value of methylated or demethylated GFRa1 is calculated by using a Receiver Operating Characteristic (ROC) curve;
   c) extracting gastric, colon or liver tissue DNA samples from test patients in vitro, detecting and calculating the proportion of methylated or demethylated GFRa1 CpG islands in the promoter region of GFRa1 of the DNA samples;
   d) comparing the proportion of methylated or demethylated GFRa1 CpG islands determined in the step c) with the cutoff value set in the step b); and
   e) detecting the occurrence of metastasis of cancers and a short postoperative survival based on the detection of a lower or equal proportion of methylated GFRa1 CpG islands determined in step c) as compared to the cutoff value set in step b), or based on the detection of a higher or equal proportion of demethylated GFRa1 CpG islands determined in step c) as compared to the cutoff value set in the step b), wherein the proportion of the methylated or demethylated GFRa1 CpG islands is determined and calculated by DHPLC, bisulfite-sequencing or fluorescent probe-based, quantitative, methylation-specific PCR (MethyLight) using oligonucleotide groups:
   i) the primer pair set forth in SEQ ID NO: 9 and SEQ ID NO: 10, and the probe set forth in SEQ ID NO: 11; or
   ii) the primer pair set forth in SEQ ID NO: 12 and SEQ ID NO: 13, and the probe set forth in SEQ ID NO: 14, and
   wherein said cancer is gastric cancer, colon cancer or liver cancer.

5. The method of detection of metastasis of cancers and cancer patients' postoperative survival in vitro according to claim 4, wherein the proportion of the methylated or demethylated CpG islands described in steps b) and c) is determined and calculated as follows: chemically modifying unmethylated cytosine so as to convert unmethylated cytosine residues in said DNA sample to uracil residues to produce modified sequences of GFRa1 CpG islands; designing and synthesizing primer sets and amplifying the methylated or demethylated GFRa1 CpG islands and determining and calculating the proportion of methylated or demethylated GFRa1 CpG islands with quantitative analysis of methylation.

6. The method of detection of metastasis of cancers and cancer patients' postoperative survival in vitro according to claim 5, wherein the modified sequences of GFRa1 islands are as shown in SEQ ID NO: 1, 2, 3 or 4.

7. A method of detection of abnormal reactivation of the GFRa1 gene comprising:
    obtaining a DNA sample;
    determining the methylation of CpG sites in the region around the GFRa1 gene transcription start site in GFRa1 nucleic acids present in the DNA sample; and
    detecting GFRa1 reactivation based on the detection of complete demethylation of CpG sites in the region around the GFRa1 gene transcription start site,
    wherein the methylation of CpG sites is determined and calculated by DHPLC, bisulfite-sequencing or fluorescent probe-based, quantitative, methylation-specific PCR (MethyLight) using oligonucleotide groups:
    a) the primer pair set forth in SEQ ID NO: 9 and SEQ ID NO. 10, and the probe set forth in SEQ ID NO: 11; or
    b) the primer pair set forth in SEQ ID NO: 12 and SEQ ID NO: 13, and the probe set forth in SEQ ID NO: 14; and
    wherein the region around the GFRa1 gene transcription start site is the region amplified by the primer pair set forth in SEQ ID NO: 9 and 10 or the primer pair set forth in SEQ ID NO: 12 and 13.

8. A method of detection of cancer, metastasis of cancers and cancer patient's postoperative survival comprising:
    obtaining a DNA sample;
    determining the methylation of CpG sites in the region around the GFRa1 gene transcription start site in GFRa1 nucleic acids present in the DNA sample;
    detecting GFRa1 reactivation based on the detection of complete demethylation of CpG sites in the region around the GFRa1 gene transcription start site, wherein GFRa1 reactivation is indicative of the occurrence of cancer, metastasis of cancers and short postoperative survival,
    wherein the methylation of CpG sites is determined and calculated by DHPLC, bisulfite-sequencing or fluorescent probe-based, quantitative, methylation-specific PCR (MethyLight) using oligonucleotide groups:
    a) the primer pair set forth in SEQ ID NO: 9 and SEQ ID NO. 10, and the probe set forth in SEQ ID NO: 11; or
    b) the primer pair set forth in SEQ ID NO: 12 and SEQ ID NO: 13, and the probe set forth in SEQ ID NO: 14;
    wherein the region around the GFRa1 gene transcription start site is the region amplified by the primer pair set forth in SEQ ID NO: 9 and 10 or the primer pair set forth in SEQ ID NO: 12 and 13, and wherein said cancer is gastric cancer, colon cancer or liver cancer.

* * * * *